(12) United States Patent
Hasegawa et al.

(10) Patent No.: US 11,173,158 B2
(45) Date of Patent: Nov. 16, 2021

(54) MEDICINAL AGENT AND BEVERAGE/FOOD FOR PREVENTING CEREBRAL DYSFUNCTION AND IMPROVING SAME

(71) Applicants: PTC Therapeutics MP, Inc., South Plainfield, NJ (US); Shiratori Pharmaceuticals Co., Ltd., Chiba (JP)

(72) Inventors: Hiroyuki Hasegawa, Tokyo (JP); Shin Aizawa, Tokyo (JP)

(73) Assignees: PTC Therapeutics MP, Inc., South Plainfield, NJ (US); Shiratori Pharmaceuticals Co., Ltd., Chiba (JP)

(*) Notice: Subject to any disclaimer, the term of this patent is extended or adjusted under 35 U.S.C. 154(b) by 0 days.

(21) Appl. No.: 16/444,396

(22) Filed: Jun. 18, 2019

(65) Prior Publication Data

US 2020/0009145 A1 Jan. 9, 2020

Related U.S. Application Data

(63) Continuation of application No. 15/823,826, filed on Nov. 28, 2017, now abandoned, which is a continuation of application No. 13/642,639, filed as application No. PCT/JP2011/002393 on Apr. 22, 2011, now abandoned.

(30) Foreign Application Priority Data

Apr. 22, 2010 (JP) ................................ 2010-098602

(51) Int. Cl.
A61K 31/519 (2006.01)
A23L 33/10 (2016.01)
A23L 2/52 (2006.01)
C07D 475/04 (2006.01)

(52) U.S. Cl.
CPC .............. A61K 31/519 (2013.01); A23L 2/52 (2013.01); A23L 33/10 (2016.08); C07D 475/04 (2013.01)

(58) Field of Classification Search
CPC .................................................. A61K 31/519
See application file for complete search history.

(56) References Cited

U.S. PATENT DOCUMENTS

| 4,550,109 A | 10/1985 | Folkers et al. |
| 4,758,571 A * | 7/1988 | Curtius .................. A61P 25/00 514/249 |
| 4,774,244 A | 9/1988 | Curtius et al. |
| 4,778,794 A * | 10/1988 | Naruse ................... A61P 43/00 514/249 |
| 9,181,254 B2 | 11/2015 | Yoshino et al. |
| 9,212,183 B2 | 12/2015 | Sieger et al. |
| 2005/0197341 A1 | 9/2005 | Woolf et al. |
| 2012/0114767 A1 | 5/2012 | Clelland et al. |
| 2013/0108694 A1 | 5/2013 | Chou et al. |
| 2013/0237543 A1 | 9/2013 | Oppenheimer et al. |
| 2017/0000793 A1 | 1/2017 | Oppenheimer et al. |
| 2017/0307591 A1 | 10/2017 | Woolf et al. |

FOREIGN PATENT DOCUMENTS

| EP | 0722731 A1 | 7/1996 |
| JP | 59-25323 | 2/1984 |
| JP | 61-1688 | 1/1986 |
| JP | H06-192100 A | 7/1994 |
| WO | WO-96/03989 A1 | 2/1996 |
| WO | WO-2006/004719 A2 | 1/2006 |
| WO | WO-2006/120176 A2 | 11/2006 |
| WO | WO-2008/89008 A2 | 7/2008 |
| WO | WO-2009/088530 A1 | 7/2009 |
| WO | WO-2018/102314 A1 | 6/2018 |
| WO | WO-2018/102315 A1 | 6/2018 |
| WO | WO-2019/046849 A1 | 3/2019 |

OTHER PUBLICATIONS

STN document accession No. 1992-51331, 1992.*
Danfors et al., "Tetrahydrobiopterin in the treatment of children with autistic disorder: a double-blind placebo-controlled crossover study." J Clin Psychopharmacol. 25(5):485-9 (2005).
Fernell et al., "Possible effects of tetrahydrobiopterin treatment in six children with autism—clinical and positron emission tomography data: a pilot study," Dev Med Child Neurol. 39(5):313-318 (1997).
Frye et al., "Metabolic effects of sapropterin treatment in autism spectrum disorder: a preliminary study." Transl Psychiatry. 3(3):e237 (2013).
Frye et al., "Tetrahydrobiopterin as a novel therapeutic intervention for autism," available in PMC Jul. 1, 2011, published in final edited form as: Neurotherapeutics. 7(3): 241-9 (2010) (15 pages).
Frye, "Central tetrahydrobiopterin concentration in neurodevelopmental disorders," Front Neurosci. 4:52 (2010).
Frye, "Tetrahydrobiopterin deficiency in autism spectrum disorder." N Am J Med Sci. 7(3):93-6 (2014).
Klaiman et al., "Tetrahydrobiopterin as a treatment for autism spectrum disorders: a double-blind, placebo-controlled trial," J Child Adolesc Psychopharmacol. 23(5): 320-8 (2013) (11 pages).

(Continued)

*Primary Examiner* — Svetlana M Ivanova
(74) *Attorney, Agent, or Firm* — Clark & Elbing LLP

(57) ABSTRACT

Disclosed is a means for improving the symptoms of a cerebral dysfunction. The present inventors made a new discovery that the activity of brain aromatic monoamines increases when sepiapterin is administered peripherally. Disclosed, therefore, is a medicinal agent, which contains at least sepiapterin or a salt thereof, for preventing or improving cerebral dysfunction. Also disclosed is a beverage/food, which contains at least sepiapterin or a salt thereof, for preventing or improving cerebral dysfunction. Unlike tetrahydrobiopterin and the like, sepiapterin can control reductions in the brain neuron levels of brain aromatic monoamines (serotonin, dopamine, noradrenaline, and the like) and increase the activity thereof even when administered peripherally. Therefore, sepiapterin may be effective for cerebral dysfunctions, which are due to reductions in the brain neuron levels of brain aromatic monoamines, such as depression, bulimia, autism, impaired consciousness and concentration, cognitive disorders and other central mental disorders, as well as myotonia, rigidity, tremors, and other central motor disorders.

8 Claims, 7 Drawing Sheets

(56) References Cited

OTHER PUBLICATIONS

Smith et al., "Exploratory study of the effect of one week of orally administered CNSA-001 (sepiapterin) on CNS levels of tetrahydrobiopterin, dihydrobiopterin and monoamine neurotransmitter metabolites in healthy volunteers." Mol Genet Metab Rep. 21:100500 (2019) (3 pages).
Naruse et al. *Neurobiology of Infantile Autism*. Proceedings of the International Symposium on Neurobiology of Infantile Autism, Nov. 10-11, Tokyo, Japan, 317-60 (1992) (41 pages).
U.S. Appl. No. 17/059,632, PTC Therapeutics MP, Inc.
U.S. Appl. No. 17/059,719, PTC Therapeutics MP, Inc.
Bruschi et al., "Strategies to modify the drug release from pharmaceutical systems." Woodhead Publishing Medical (2015).
Wikipedia, "Cerebrospinal fluid," <https://en.wikipedia.org/w/index.php?title=Cerebrospinal_fluid&oldid=836321065>, retrieved Aug. 5, 2019: entire document (2018) (8 pages).
Hahn et al., "Myotonic disorders: A review article," Iran J Neurol. 15(1): 46-53 (2016).
Meola et al., "Reduced cerebral blood flow and impaired visual-spatial function in proximal myotonic myopathy," Neurology. 53(5): 1042-50 (1999) (11 pages).
Anastasiadis et al., "Tetrahydrobiopterin uptake into rat brain synaptosomes, cultured PC12 cells, and rat striatum," Brain Res. 665(1): 77-84 (1994).
Beaumont et al., "Design of ester prodrugs to enhance oral absorption of poorly permeable compounds: challenges to the discovery scientist," Curr Drug Metab. 4(6): 461-85 (2003).
Bosker et al., "Biochemical and behavioral effects of long-term citalopram administration and discontinuation in rats: role of serotonin synthesis," Neurochem Int. 57(8): 948-957 (2010).
Brand et al., "Neurochemical effects following peripheral administration of tetrahydropterin derivatives to the hph-1 mouse," J Neurochem. 66(3): 1150-6 (1996).
Curtius et al., "Successful treatment of depression with tetrahydrobiopterin," Lancet. 1(8325): 657-8 (1983).
Fukushima et al., "Analysis of reduced forms of biopterin in biological tissues and fluids," Anal Biochem. 102(1): 176-88 (1980).
Hasegawa et al., "Delivery of exogenous tetrahydrobiopterin (BH4) to cells of target organs: role of salvage pathway and uptake of its precursor in effective elevation of tissue BH4," Mol Genet Metab. 86(Suppl 1): S2-10 (2005).
Hasegawa et al., "Iron dependence of tryptophan hydroxylase activity in RBL2H3 cells and its manipulation by chelators," Eur J Biochem. 261(3): 734-9 (1999).
Hasegawa et al., Recent studies on sepiapterin and biopterin transport in mammalian cells, In proceedings of 13th international symposium on chemistry & biology of pteridines & folates, Blau, N. and Thony, B. eds, SPS Verlagsgesellschaft mbH. Heibronn, Germany, pp. 254-268, 2007.
Hasegawa et al., Tryptophan Hydroxylase and Serotonin Synthesis Regulation, *Handbook of Behavioral Neuroscience*, Eds. P.M.1. Christian, L.J, Barry, Elsevier, pp. 183-202 (2010).
Inoue et al., "Distribution of 5-hydroxytryptamine (5HT) in tissue of a mutant mouse deficient in mast cell (W/Wv). Demonstration of the contribution of mast cells to the 5HT content in various organs," Agents Actions. 16(5): 295-301 (1985).
International Preliminary Report on Patentability for International Application No. PCT/JP2011/002393, dated Mar. 28, 2012 (6 pages).
International Search Report for International Application No. PCT/JP2011/002393, dated Jun. 15, 2011 (6 pages).
Kapatos et al., "Biosynthesis of biopterin by rat brain," J Neurochem. 39(4): 1152-62 (1982).
Kaufman, "On the structure of the phenylalanine hydroxylation cofactor," J Biol Chem. 237(8): 2712-3 (1962).
Kaufman, "Studies on the structure of the primary oxidation product formed from tetrahydropteridines during phenylalanine hydroxylation," J Biol Chem. 239: 332-8 (1964).
Kettler et al., "In vivo enhancement of tyrosine hydroxylation in rat striatum by tetrahydrobiopterin," Nature. 249(456): 476-8 (1974).
Koshimura et al., "6R-L-erythro-5,6,7,8-tetrahydrobiopterin: a regulator of neurotransmitter release," Adv Exp Med Biol. 338: 313-9 (1993).
Koshimura et al., "Characterization of a dopamine-releasing action of 6R-L-erythro-tetrahydrobiopterin: comparison with a 6S form," J Neurochem. 65(2): 827-830 (1995).
Koshimura et al., "Dopamine-releasing action of 6R-L-erythro-tetrahydrobiopterin: analysis of its action site using sepiapterin," J Neurochem. 63(2): 649-654 (1994).
Koshimura et al., "Enhancement of dopamine release in vivo from the rat striatum by dialytic perfusion of 6R-L-erythro-5,6,7,8-tetrahydrobiopterin," J Neurochem. 54(4): 1391-7 (1990).
Koshimura et al., "The role of 6R-tetrahydrobiopterin in the nervous system," Prog Neurobiol. 61(4): 415-38 (2000).
Levine et al., "Entrance of tetrahydropterin derivatives in brain after peripheral administration: effect on biogenic amine metabolism," J Pharmacol Exp Ther. 242(2): 514-22 (1987).
Liang et al., "The regulation of dopamine release from striatum slices by tetrahydrobiopterin and L-arginine-derived nitric oxide," Brain Res. 800(2): 181-6 (1998).
Manji et al., "The cellular neurobiology of depression," Nat Med. 7(5): 541-7 (2001).
Massey et al., Flavin and Pteridine Monooxygenases, *The Enzymes*. 3rd Ed. vol. 12, pp. 191-252, Academic Press. Inc. NY (1975).
McHugh et al., "The tetrahydrobiopterin pathway: a novel target for the treatment of depression," Pharmacogenomics. 12(12): 1625-7 (2011).
Miwa et al., "6R-L-erythro-5,6,7,8-tetrahydrobiopterin as a regulator of dopamine and serotonin biosynthesis in the rat brain," Arch Biochem Biophys. 239(1): 234-41 (1985).
Niederwieser et al., "Atypical phenylketonuria with defective biopterin metabolism. Monotherapy with tetrahydrobiopterin or sepiapterin, screening and study of biosynthesis in man," Eur J Pediatr. 138(2): 110-2 (1982).
Ohashi et al., "Membrane transport of sepiapterin and dihydrobiopterin by equilibrative nucleoside transporters: a plausible gateway for the salvage pathway of tetrahydrobiopterin biosynthesis," Mol Genet Metab. 102(1): 18-28 (2011).
Ohashi et al., "Organic anion transporters, OAT1 and OAT3, are crucial biopterin transporters involved in bodily distribution of tetrahydrobiopterin and exclusion of its excess," Mol Cell Biochem. 435(1-2): 97-108 (2017).
Ohue et al., "A novel action of 6R-L-erythro-5,6,7,8-tetrahydrobiopterin, a cofactor for hydroxylases of phenylalanine, tyrosine and tryptophan: enhancement of acetylcholine release in vivo in the rat hippocampus," Neurosci Lett. 128(1):93-96 (1991).
Ohue et al., "Enhancement of acetylcholine release in the hippocampus by 6R-L-erythro-5,6,7,8-tetrahydrobiopterin is mediated by 5-hydroxytryptamine," Brain Res. 607(1-2): 255-60 (1993).
Ohue et al., "Monoamine-mediated enhancement of acetylcholine release in rat hippocampus by 6R-L-erythro-5,6,7,8-tetrahydrobiopterin," Brain Res. 570(1-2): 173-9 (1992).
Pfleiderer, "Überführung von biopterin in sepiapterin und absolute konfiguration des sepiapterins," Chemische Berichte. 112: 2750-2755 (1979).
Porsolt et al., "Depression: a new animal model sensitive to antidepressant treatments," Nature. 266(5604): 730-2 (1977).
Sansone et al., "SSRI-Induced Indifference," Psychiatry (Edgmont). 7(10): 14-18 (2010).
Sawabe et al., "Cellular uptake of sepiapterin and push-pull accumulation of tetrahydrobiopterin," Mol Genet Metab. 94(4): 410-6 (2008).
Sawabe et al., "Tetrahydrobiopterin uptake in supplemental administration: elevation of tissue tetrahydrobiopterin in mice following uptake of the exogenously oxidized product 7,8-dihydrobiopterin and subsequent reduction by an anti-folate-sensitive process," J Pharmacol Sci. 96(2): 124-33 (2004).
Sawabe et al., Sepiapterin administration raises tissue BH4 levels more efficiently than BH4 supplement in normal mice, *Chemistry and Biology of Pteridines and Folates*. Ed. Milstien et al., pp. 199-204 (2001).

(56) References Cited

OTHER PUBLICATIONS

Sawada et al., "Tryptophan hydroxylase activity in the brains of controls and parkinsonian patients," J Neural Transm. 62(1-2): 107-15 (1985).
Shiraki et al., "Stimulating effect of 6R-tetrahydrobiopterin on Ca2+ channels in neurons of rat dorsal motor nucleus of the vagus," Biochem Biophys Res Commun. 221(1): 181-5 (1996).
Siesser et al., "Chronic SSRI treatment exacerbates serotonin deficiency in humanized Tph2 mutant mice." ACS Chem Neurosci. 4(1): 84-8 (2013).
Tsuji et al., "Evaluation methods for general and depressive-like behaviors," Folia Pharmacol. Jpn. 130: 97-104 (2007).
Vásquez-Vivar et al., "Tetrahydrobiopterin in the prevention of hypertonia in hypoxic fetal brain," Ann Neurol. 66(3): 323-31 (2009).
Woggon et al., "Unsuccessful treatment of depression with tetrahydrobiopterin," Lancet. 2(8417-8418): 1463 (1984).
Wolf et al., "Effect of tetrahydrobiopterin on serotonin synthesis, release, and metabolism in superfused hippocampal slices," J Neurochem. 57(4): 1191-7 (1991).
Written Opinion for International Application No. PCT/JP2011/002393, dated Jun. 28, 2011 (5 pages).
Yamamoto et al., "A comparison of sepiapterin and tetrahydrobiopterin uptake by RBL2H3 cells," Pteridines. 7(4): 154-156 (1996).
Zahodne et al., "Are selective serotonin reuptake inhibitors associated with greater apathy in Parkinson's disease?," J Neuropsychiatry Clin Neurosci. 24(3): 326-30 (2012).
Zorzi et al., "Detection of sepiapterin in CSF of patients with sepiapterin reductase deficiency," Mol Genet Metab. 75(2): 174-7 (2002).

\* cited by examiner

[Fig.1]
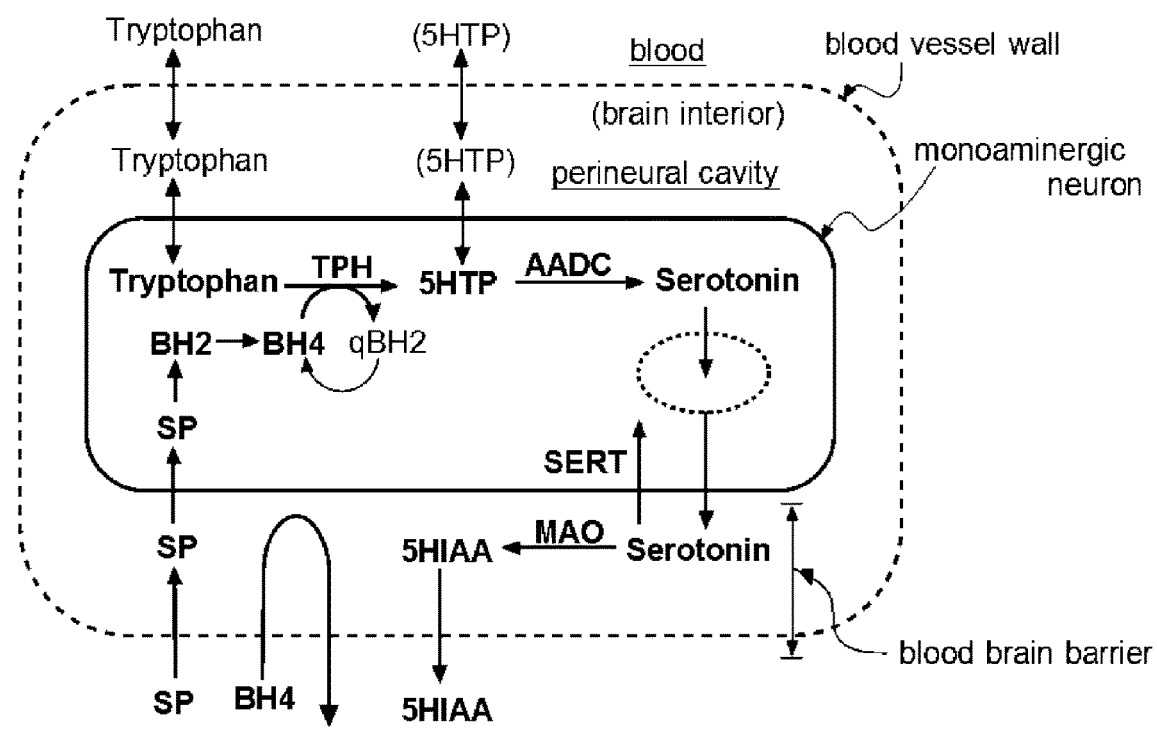

[Fig.2A]
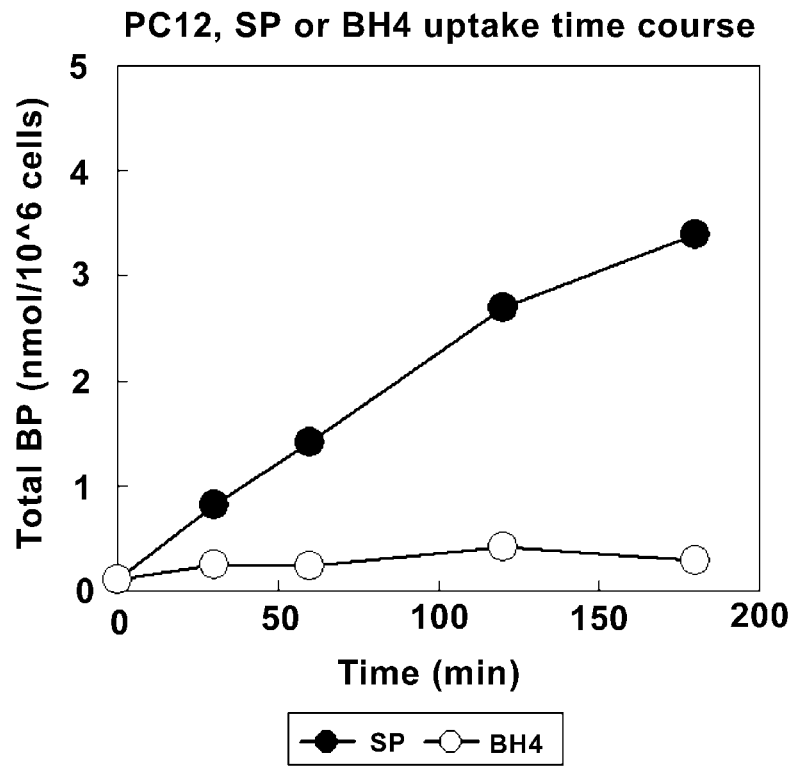
[Fig.2B]
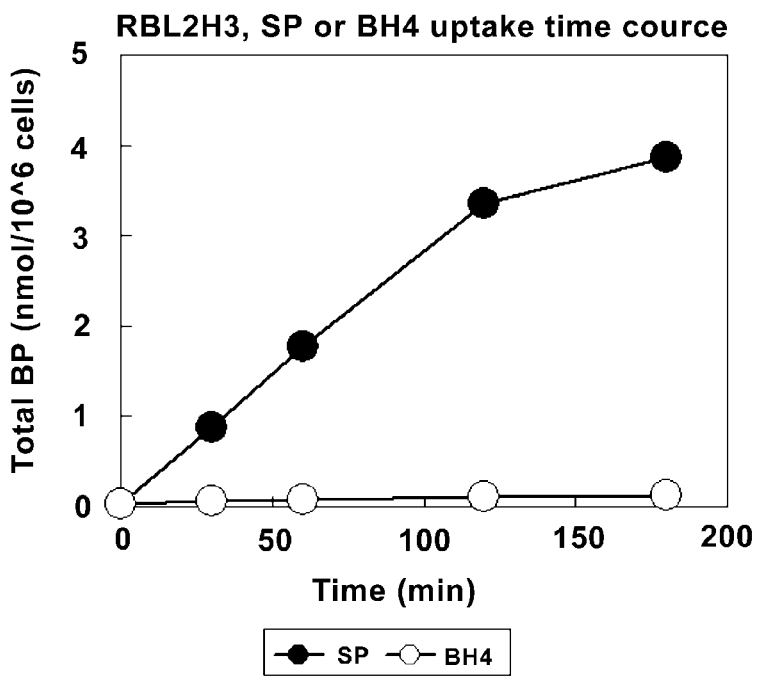

[Fig.3]
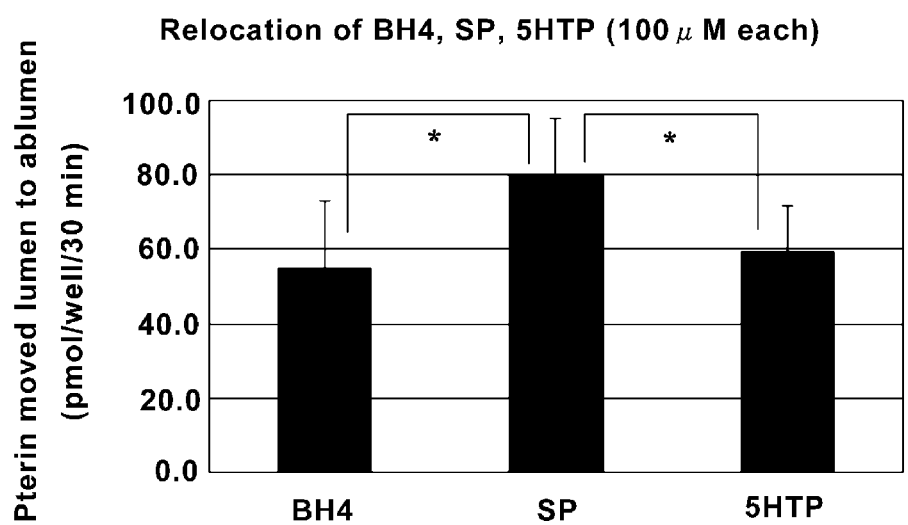

[Fig.4A]
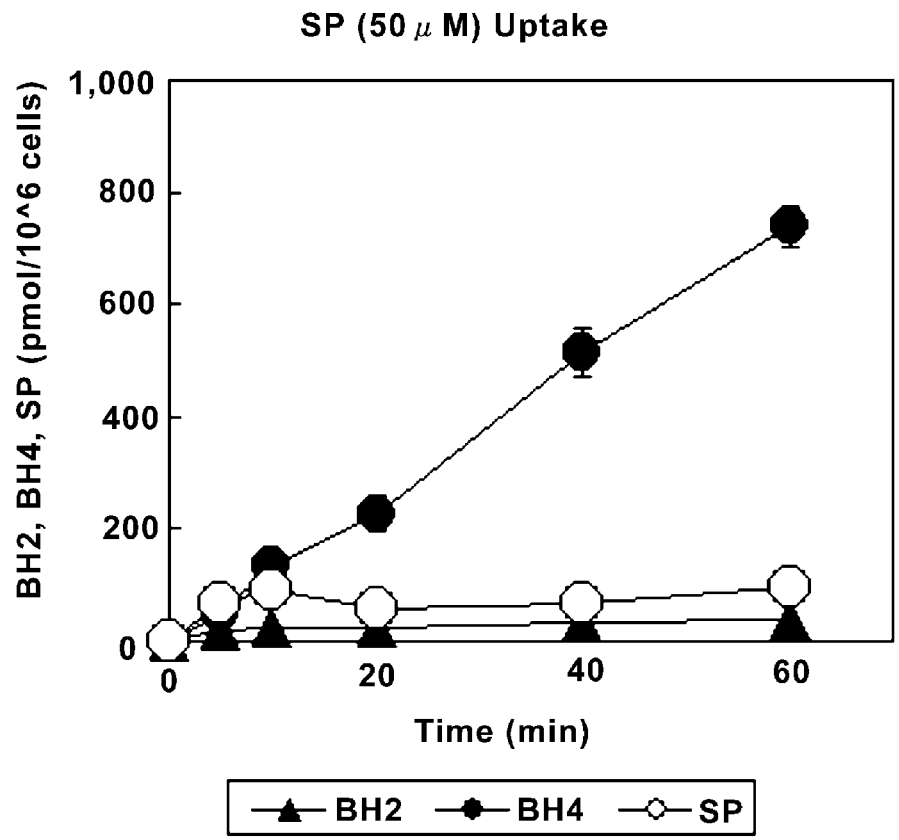
[Fig.4B]
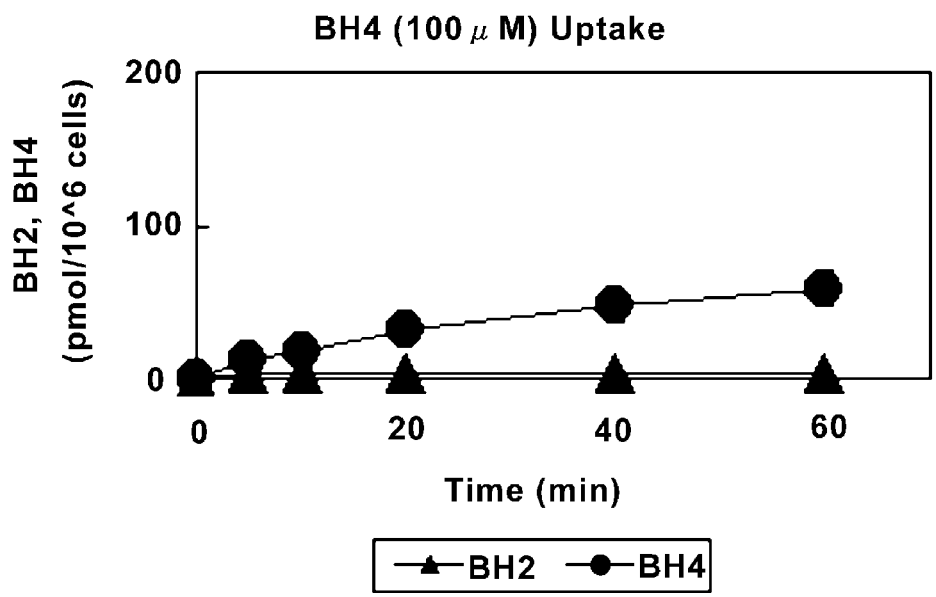

[Fig.5A]
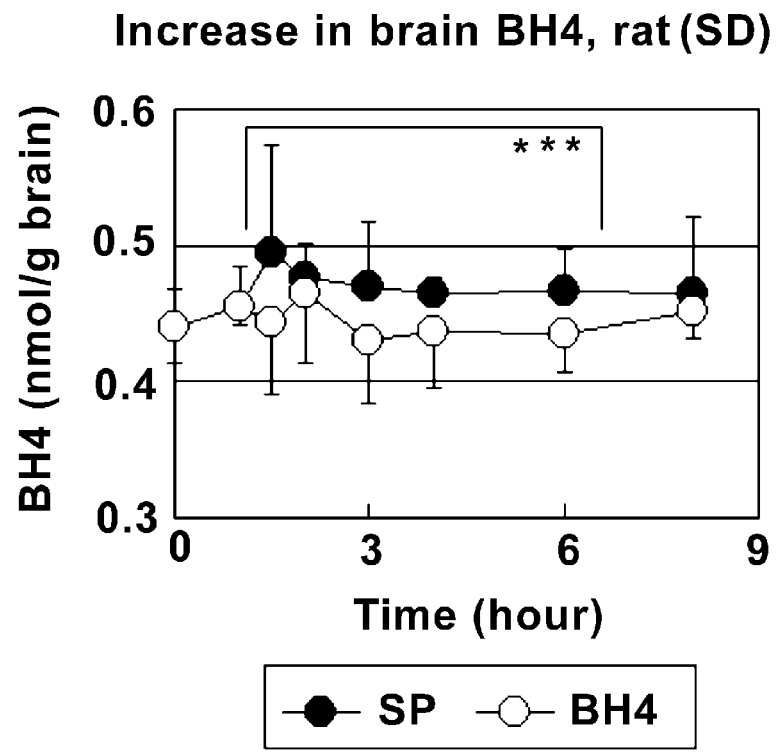
[Fig.5B]
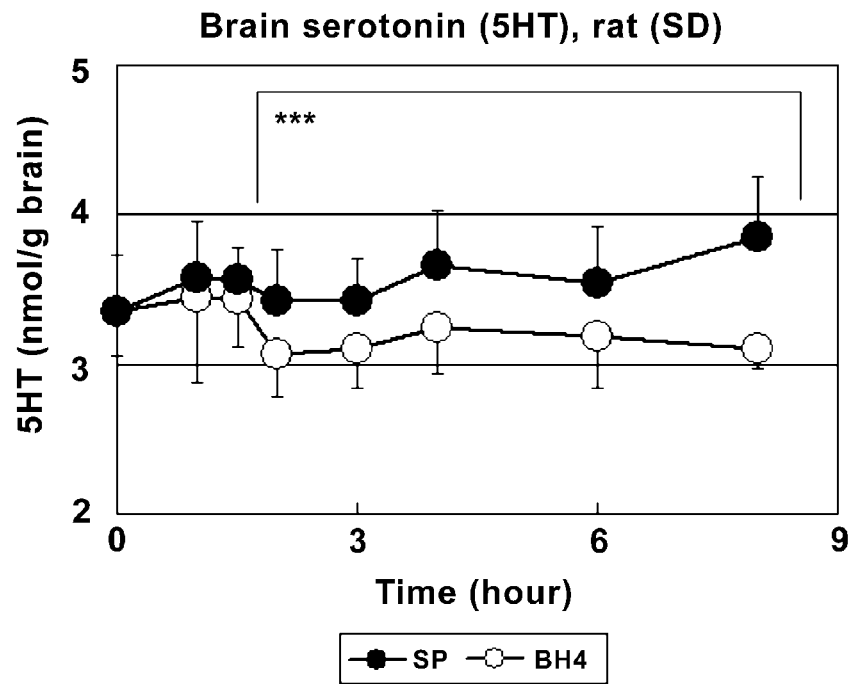

[Fig.5C]
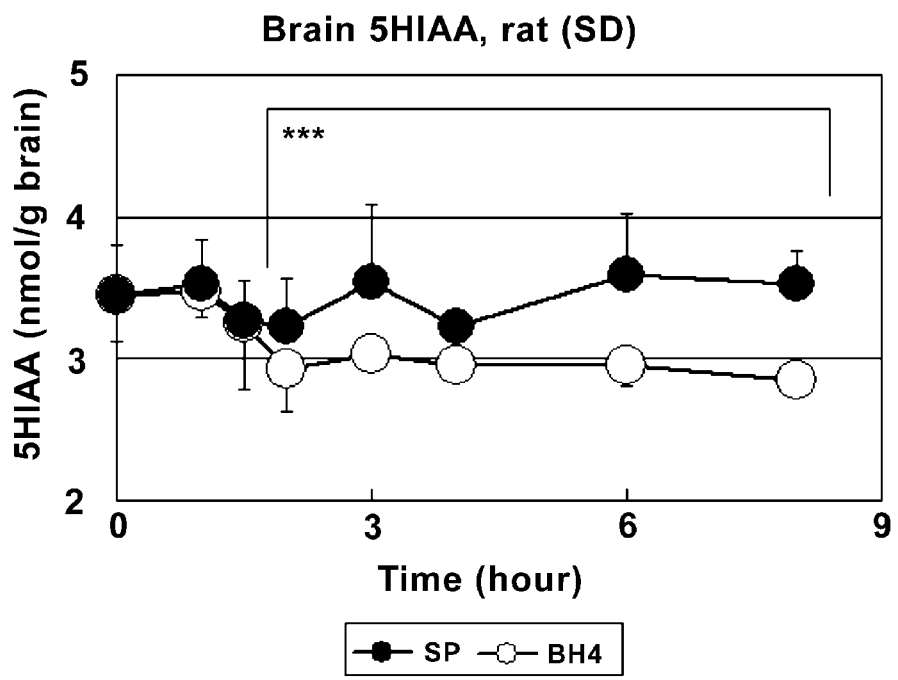
[Fig.6]
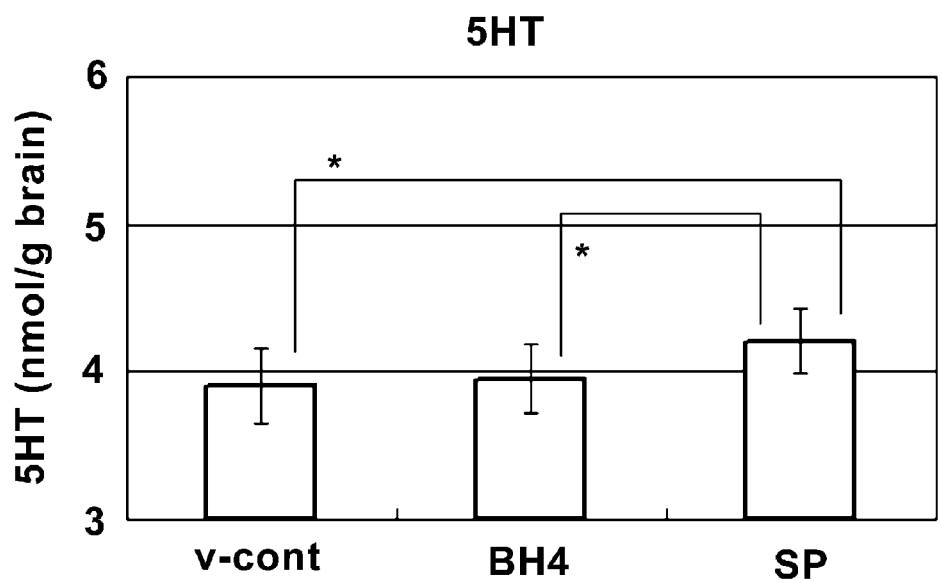

[Fig.7]
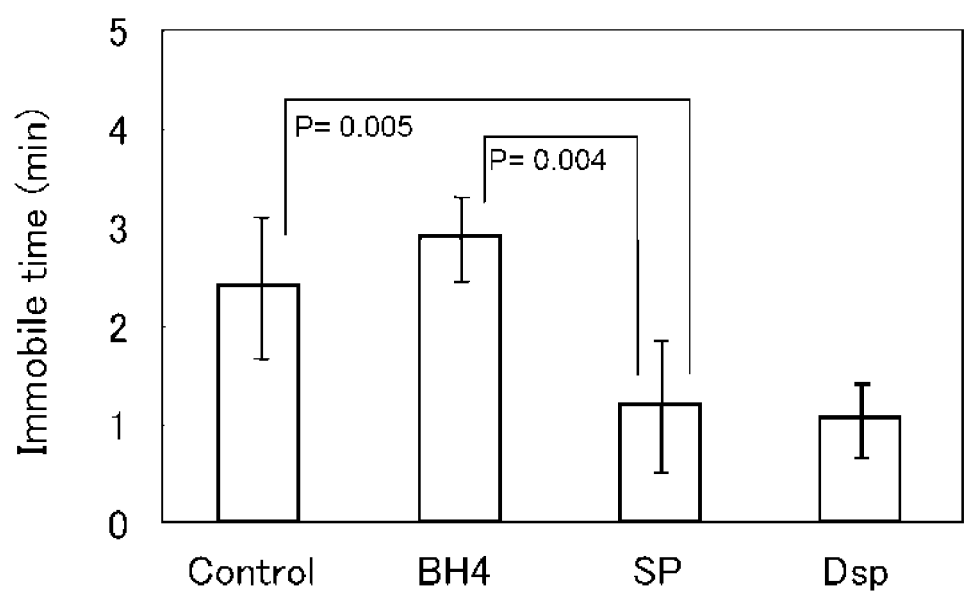

MEDICINAL AGENT AND BEVERAGE/FOOD FOR PREVENTING CEREBRAL DYSFUNCTION AND IMPROVING SAME

FIELD OF THE INVENTION

The present invention relates to a drug and food/drink which contain sepiapterin for preventing or improving cerebral dysfunction. More specifically, the present invention relates to a drug and food/drink for preventing, improving and treating diseases in which neurotransmitters in the brain are involved, for example, central mental disorders (such as depression, hyperphagia, autism, impaired consciousness and concentration, and cognitive disturbance) or central motor disorders (such as myotonia, rigidity and tremor).

BACKGROUND ART

The brain is the highest center of information transmission via nerves such as motor and consciousness, playing an important role in human mental activities such as feeling, emotion and reason as well as optional control of motor. The brain is constructed with an innumerable number of neurons, and information between the neurons is transmitted by neurotransmitters in the brain.

A monoamine neurotransmitter is a generic name for any non-amino acid neurotransmitter which contains one amino group. Among these monoamine neurotransmitters, a monoamine neurotransmitter biosynthesized in the body from tyrosine or tryptophan of a naturally occurring L-amino acid as a precursor is referred to as an aromatic monoamine. Representative aromatic monoamines include serotonin, noradrenaline, dopamine and adrenaline. Aromatic monoamines are present in the brain and peripheries as well. It is known that aromatic monoamines present in the brain play an important role in transmitting information in the brain and are also deeply involved in control of mental activities, emotion and motor.

Serotonin is an aromatic monoamine which is commonly contained in plants and animals including humans and primarily present in chromaffin cells of mucous membranes of the small intestine and in platelets, etc. Serotonin is also partially present in the central nervous system. This substance functions as a neurotransmitter in the central nervous system. Serotonin nerves extend their nerve fibers diversely from nuclei raphes of the medullary to the brain and spinal cord including the hypothalamus, basal ganglion and corpus striatum, thereby greatly influencing mental activities of humans such as emotion, fatigue, pain and appetite.

In recent years, a correlation has been found between serotonin and cerebral dysfunction such as depression, hyperphagia, autism, impaired consciousness and concentration, and cognitive disturbance. It is now possible to improve symptoms of cerebral dysfunction to some extent by means of drugs acting on a serotonin system. For example, an SSRI (Serotonin Selective Reuptake Inhibitor) is now commercially available as a drug which inhibits reabsorption of serotonin released from synapses, thereby improving symptoms of depression, etc. However, it has been pointed out that since an SSRI decreases the total amount of serotonin in neurons, the drug may further exacerbate symptoms of depression for longer administration.

Noradrenaline is an aromatic monoamine which is widely present at sympathetic nerve endings and in the central nervous system and also a precursor of adrenaline. This substance works as an adrenocortical hormone and a neurotransmitter at the peripheries. On the other hand, noradrenaline nerves of the locus ceruleus project throughout the brain and it is thought that these are involved in attention, drive impulse, etc. A correlation has also been found with a change in the noradrenaline system with depression.

An SNRI (Serotonin and Norepinephrine Reuptake Inhibitor) is a drug which inhibits reabsorption of serotonin and noradrenaline in a synapse, thereby increasing concentration of the neurotransmitters at perineural cavities to improve symptoms of depression. It is thought that this drug not only increases the concentration of serotonin to improve symptoms of depression but also inhibits reabsorption of noradrenaline to stimulate sympathetic nerves, thereby exhibiting effects of enhancing ambition and feeling. However, as in the case of an SSRI, it has been pointed out that an SNRI also decreases the total amount of serotonin in neurons and may exacerbate symptoms of depression on longer administration.

Dopamine is an aromatic monoamine present in the central nervous system and also a precursor of adrenaline and noradrenaline. In the brain, the brainstem ventral tegmental area and nigral dopamine nerves project on the cerebrum frontal lobe, corpus striatum, etc., and are involved in control of motor, regulation of hormones, feelings of pleasure, motivation, learning, etc.

In Parkinson's disease, the nigrostriatal dopamine nerves are decreased to cause motor symptoms such as muscle rigidity, tremor and akinesia. There is an assumption that links dopamine with some forms of schizophrenia and depression.

Of aromatic monoamines, some are present in peripheral cells, etc., are present in neurons of the central nervous system. In principle, aromatic monoamines in the brain do not pass through the blood-brain barrier but they are synthesized and metabolized independently. That is, no mutual migration or complementation occurs between the aromatic monoamines present in peripheral cells and the aromatic monoamines present in neurons of the central nervous system.

Aromatic monoamine nerves in the brain release aromatic monoamines (such as serotonin, noradrenaline and dopamine) stored in releasing granules in cells. After being released, the aromatic monoamines are subjected to reuptake by individual neurons, mixed with newly bio-synthesized aromatic monoamines and taken up again into the releasing granules. This mechanism is repeated in a recycling manner, and before being taken up into the releasing granules, some of the aromatic monoamines are metabolized in the cells to produce inactive metabolic products. Aromatic monoamines will not flow into the brain or flow out from the brain due to functions of the blood-brain barrier. However, their metabolic products are discharged from the brain into the peripheries. Furthermore, aromatic amino acids (such as tryptophan and tyrosine) which are immediate precursors of aromatic monoamine biosynthesis will pass through the blood-brain barrier.

Tetrahydrobiopterin (BH4) is a coenzyme of phenylalanine hydroxylase, tyrosine hydroxylase, tryptophan hydroxylase and nitric oxide synthase. This substance is a coenzyme which is essential for enzymatic reactions such as reactions for synthesis of tyrosine from phenylalanine, synthesis of serotonin from tryptophan, synthesis of dopa from tyrosine and synthesis of nitric oxide and citrulline from arginine.

The above-described enzymes are incapable of exhibiting catalytic actions sufficiently, if cells are deficient in tetrahydrobiopterin. This causes hyperphenylalaninemia and reduction in bioavailability of monoamine neurotransmitters such as dopamine, noradrenaline and serotonin.

Diseases caused by defective production of tetrahydrobiopterin include malignant hyperphenylalaninemia and Segawa disease (dopa-responsive dystonia). Furthermore, such a possibility has been suggested that abnormal metabolism of tetrahydrobiopterin may be responsible for or exacerbate depression, hyperphagia, Parkinson's disease, autism, schizophrenia, etc.

In cases where tetrahydrobiopterin is transmitted from the peripheries to the brain, a part of tetrahydrobiopterin is slightly captured by brain tissues but rapidly discharged outside of brain tissues at a stage that it does not reach aromatic monoamine neurons. That is, tetrahydrobiopterin is extremely difficult in passing through the blood-brain barrier.

"7,8-Dihydro-6-[(S)-2-hydroxy-1-oxopropyl]-pterin (trivial name: sepiapterin, hereinafter referred to as sepiapterin)" is an endogenous compound which widely occurs as an animal pigment in a variety of animals including humans and also contained in daily foods in trace amounts. In 1960, Nawa determined a chemical structure of sepiapterin as one of the pigments contained in the eyes of a drosophila.

Nothing is so far known about bioactivity of sepiapterin in the human body. Sepiapterin is inevitably produced in the human body by auto-oxidation of tetrahydro-6-lactoyl-tetrahydropterin (an intermediate in the synthesis of tetrahydrobiopterin from GTP). However, this substance amounts in trace and is nearly undetectable in blood or urine.

It is known that sepiapterin is easily taken up into animal cells and converted to tetrahydrobiopterin through two-step enzymatic reactions by SPR (Sepiapterin Reductase) and DHFR (Dihydrofolate Reductase) (refer to Non-Patent Document 1, for example).

In recent years, cell membrane permeation characteristics of tetrahydrobiopterin, its metabolic product and a prodrug (such as sepiapterin or dihydrobiopterin) are in the process of being more clearly understood. For example, Non-Patent Document 2 has disclosed findings on cell membrane transport of a pterin compound.

There have been proposed a variety of drugs for treating various diseases which contain tetrahydrobiopterin, etc. For example, Patent Document 1 has disclosed a pterin-derivative containing drug for treating depression and Parkinson's disease, Patent Document 2 has disclosed a tetrahydrobiopterin-containing composition for treating attention deficit hyperactivity disorders and hyperphenylalaninemia, Patent Document 3 has disclosed a drug having tetrahydrobiopterin as an active ingredient for treating spinocerebellar degeneration, and Patent Document 4 has disclosed a cancer metastasis depressant having a pterin derivative as an active ingredient. Furthermore, in Non-Patent Document 3, evaluation has been made for monotherapy with tetrahydrobiopterin or sepiapterin given to patients with biopterin metabolism deficiency phenylketonuria. In Non-Patent Document 4, evaluation has been made for biosynthesis of biopterin in the brain of a rat. In Non-Patent Document 5, it has been demonstrated that aromatic monoamines in the brain are increased in concentration only on peripheral administration of tetrahydrobiopterin at a dose close to a lethal dose. Furthermore, Non-Patent Document 6 is literature covering formulation of a prodrug to be described below, Non-Patent Document 7 is literature covering synthesis of sepiapterin to be described below, Non-Patent Document 8 is literature covering the Fukushima-Nixon method to be described below, Non-Patent Document 9 is literature covering a method for measuring amounts of serotonin, 5-hydroxytryptophan and 5-hydroxyindole acetic acid.

[Patent Document 1] Japanese published Unexamined Patent Application No. JP59-25323 A1
[Patent Document 2] Japanese Translation of International Application (Kohyo) No. JP2008-504295 A1
[Patent Document 3] WO96/03989
[Patent Document 4] Japanese published Unexamined Patent Application No. JP06-192100 A1
[Non-Patent Document 1] K. Sawabe, K. Yamamoto, Y. Harada, A. Ohashi, Y. Sugawara, H. Matsuoka, and H. Hasegawa, "Cellular uptake of sepiapterin and push-pull accumulation of tetrahydrobiopterin." Mol Genet Metab 94 (2008) 410-416.
[Non-Patent Document 2] H. Hasegawa, K. Sawabe, N. Nakanishi, and O. K. Wakasugi, "Delivery of exogenous tetrahydrobiopterin (BH4) to cells of target organs: role of salvage pathway and uptake of its precursor in effective elevation of tissue BH4." Mol Genet Metab 86 Suppl 1 (2005) S2-10.
[Non-Patent Document 3] A. Niederwieser, H.-Ch. Curtius, M. Wang and D. Leupold, "Atypical phenylketonuria with defective biopterin metabolism. Monotherapy with tetrahydrobiopterin or sepiapterin, screening und study of biosynthesis in man.": Eur J Pediatr (1982) 138: 110-112.
[Non-Patent Document 4] G. Kapatos, S. Katoh and S. Kaufman, "Biosynthesis of biopterin by rat brain.": Journal of Neurochem. 39, 1152-1162 (1982).
[Non-Patent Document 5] M. P. Brand, K. Hyland, T. Engle, I. Smith and S. J. R. Heales, "Neurochemical effects following peripheral administration of tetrahydropterin derivatives to the hph-1 mouse.": Journal of Neurochem. 66, 1150-1156 (1996).
[Non-Patent Document 6] K. Beaumont, R. Webster, I. Gardner, K. Dack, "Design of ester prodrugs to enhance oral absorption of poorly permeable compounds: challenges to the discovery scientist.": Current Drug Metabolism (2003), 4(6), 461-485
[Non-Patent Document 7] W. Pfleiderer, "Pteridine, LXVIII. Uberfuhrung von Biopterin in Sepiapterin und absolute Konfiguration des Sepiapterins (Konfiguration Des Sepiapterins).": Chemische Berichte 112 (1979) 2750-2755.
[Non-Patent Document 8] T. Fukushima and J. C. Nixon, "Analysis of reduced forms of biopterin in biological tissues and fluids": Analytical Biochemistry 102, 176-188 (1980)
[Non-Patent Document 9] F. Inoue, H. Hasegawa, M. Nishimura, M. Yanagisawa and A. Ichiyama, "Distribution of 5-hydroxytryptamine (5HT) in tissue of a mutant mouse deficient in mast cell (W/Wv). Demonstration of the contribution of mast cells to the 5HT content in various organs": Agents Actions 16, 2950301(1985)

DISCLOSURE OF THE INVENTION

Problem to be Solved by the Invention

As described above, trials have been so far made for peripherally administering tetrahydrobiopterin to improve symptoms of diseases caused by defective production of tetrahydrobiopterin.

However, peripheral administration of tetrahydrobiopterin facilitates metabolism of phenylalanine, synthesis of aromatic monoamines and synthesis of nitric oxide at the peripheries but hardly facilitates biosynthesis of monoamine neurotransmitters in the brain. This is assumed to be due to the fact that tetrahydrobiopterin hardly passes through the blood-brain barrier and is less likely to pass through cell membranes of aromatic monoamine neurons, even if a small amount of tetrahydrobiopterin reaches the brain.

Therefore, tetrahydrobiopterin is effective in facilitating metabolism of phenylalanine, synthesis of aromatic monoamines and synthesis of nitric oxide at the peripheries but not effective in facilitating synthesis of aromatic monoamines in the brain. That is, in cerebral dysfunction such as depression, hyperphagia, autism, impaired consciousness and concentration, and cognitive disturbance, tetrahydrobiopterin administration hardly improves their symptoms in reality, and is also not practically viable.

Under these circumstances, an object of the present invention is to provide new means for improving symptoms of cerebral dysfunction, for example, central mental disorders (such as depression, hyperphagia, autism, impaired consciousness and concentration, and cognitive disturbance) and central motor disorders (such as myotonia, rigidity and tremor).

Means for Solving the Problems

The inventor has newly found that sepiapterin passes through the blood-brain barrier on peripheral administration of sepiapterin and is taken up into neurons in the brain and also facilitates production of aromatic monoamines in the brain, thereby increasing their bioavailability.

Under these circumstances, the present invention provides a drug which contains at least one of sepiapterin and its salt for preventing or improving cerebral dysfunction, and the invention further provides a food and or drink which contains at least one of sepiapterin and its salt for preventing or improving cerebral dysfunction.

Unlike tetrahydrobiopterin, etc., sepiapterin is capable of preventing decrease in the levels of aromatic monoamines in the brain (for example, any one of or a plurality of serotonin, dopamine and noradrenaline) in neurons in the brain on peripheral administration and also increasing the bioavailability. Therefore, sepiapterin may be effective against cerebral dysfunction arising from decreased levels of aromatic monoamines in neurons in the brain, for example, central mental disorders such as depression, hyperphagia, autism, impaired consciousness and concentration, and cognitive disturbance or central motor disorders such as myotonia, rigidity and tremor.

A mechanism by which the bioavailability of aromatic monoamines in the brain increases by sepiapterin is assumed to be as follows. After peripheral administration, sepiapterin passes through the blood-brain barrier more easily than tetrahydrobiopterin and reaches neurons in the brain by a certain amount. Unlike tetrahydrobiopterin, sepiapterin permeates through cell membranes of neurons in the brain by facilitated transport and is taken up into cells. In the neurons in the brain, sepiapterin is converted to tetrahydrobiopterin through two-step enzymatic reactions by SPR (Sepiapterin Reductase) and DHFR (Dihydrofolate Reductase) present in the cells. Thereby, tetrahydrobiopterin in neurons in the brain is increased in amount, facilitating biosynthesis of aromatic monoamines in the brain and elevating the intracellular level of aromatic monoamines in the brain, thus resulting in an increase in the bioavailability.

In the case of tetrahydrobiopterin, even if tetrahydrobiopterin reaches the brain in a small amount through the blood-brain barrier on peripheral administration, it will not be easily taken up into neurons. This is fundamentally different in action mechanism from sepiapterin.

Effects of the Invention

The present invention may be capable of improving symptoms of various types of cerebral dysfunction.

BEST MODES FOR CARRYING OUT THE INVENTION

<Action Mechanism of the Present Invention>

With reference to FIG. 1, an explanation will be made for an action mechanism of sepiapterin of the present invention in the brain.

FIG. 1 is an illustration which depicts a metabolic system of aromatic monoamines in neurons in the brain. It is noted that FIG. 1 addresses a metabolic system of serotonin as an example. However, other aromatic monoamines such as dopamine and noradrenaline produced from dopamine are also essentially the same in metabolic system.

Substances necessary for neurons in the brain such as nutrients, humoral regulators and physiologically active substances are supplied from the blood stream (as "blood" in FIG. 1, and the same shall apply hereinafter) across the blood-brain barrier ("blood-brain barrier" in FIG. 1, and the same shall apply hereinafter) to neurons (a site described as "monoaminergic neuron" in FIG. 1, and the same shall apply hereinafter).

The blood-brain barrier is mainly constituted of (1) a blood vessel wall in the brain ("blood vessel wall" in FIG. 1, and the same shall apply hereinafter), (2) a glia cell in the perineural cavity ("perineural cavity" in FIG. 1, a region between a blood vessel wall and a neuron, the same shall apply hereinafter), etc. As described above, migration of substances, drugs, etc., in the blood stream to the brain is strictly restricted by the blood-brain barrier and only limited compounds are allowed to migrate to the brain. Compounds in the brain are also strictly restricted for discharge by the blood-brain barrier. Only limited metabolites and metabolic products are principally discharged from the brain.

A substance whose migration to neurons in the brain is restricted by the blood-brain barrier is discharged (1) by active outward transport at blood vessel walls and glia cells after reaching the vicinity of a neuron by physico-chemical diffusion, or discharged (2) from the vicinity of the neuron by finally returning to the blood stream of the brain without being taken up into the neuron after reaching the vicinity of the neuron.

On the other hand, a substance taken up into neurons in the brain reaches the neurons first at the perineural cavity (1) by physico-chemical permeation and diffusion at cell membranes or cellular gaps of glia cells, etc., or (2) by cooperative mediation of a transporter protein group present in the glia cells.

Next, a substance which has reached a neuron is taken up into the neuron (1) by physico-chemical permeation and diffusion at the cell membrane of the neuron or (2) by cooperative mediation of a transporter protein group present in the neuron. In general, since the concentration of each substance in a neuron is determined for each substance, a substance which has been taken up into the neuron and thereafter rapidly metabolized is further taken up continuously depending on an amount that has been metabolized.

Metabolism of aromatic monoamines undergoes in aromatic monoaminergic neurons in the brain ("monoaminergic neuron" in FIG. 1 and the same shall apply hereinafter).

For example, serotonin ("Serotonin" in FIG. 1 and the same shall apply hereinafter) is metabolized by the following mechanism as shown in FIG. 1. First, tryptophan of L-amino acid ("Tryptophan" in FIG. 1 and the same shall apply hereinafter) is taken up from the blood stream via the blood-brain barrier into the monoaminergic neuron. This tryptophan is converted to 5-hydroxytryptophan ("5HTP" in FIG. 1 and the same shall apply hereinafter) by actions of tryptophan hydroxylase ("TPH" in FIG. 1 and the same shall apply hereinafter) and a coenzyme thereof, that is, tetrahydrobiopterin ("BH4" in FIG. 1 and the same shall apply hereinafter) and further converted to serotonin by the action of aromatic amino acid decarboxylase ("AADC" in FIG. 1 and the same shall apply hereinafter). Serotonin biosynthesis rate-limited at the step of reaction with tryptophan hydroxylase (TPH).

It is noted that 5-hydroxytryptophan (5HTP) is a substance which is now used as the drug of first choice on peripheral administration to a patient with tetrahydrobiopterin deficiency for the purpose of increasing the amount of serotonin in the brain. It is known that, as with tryptophan, 5-hydroxytryptophan is taken up into an aromatic monoaminergic neuron from the blood stream via the blood-brain barrier on peripheral administration.

Biosynthesized serotonin is taken up into neurotransmitter-releasing granules in an aromatic monoaminergic neuron and released outside of the cell. However, serotonin does not migrate to the blood stream but remains in the brain and (1) is again taken up into the releasing granules in the aromatic monoaminergic neuron mediated by a serotonin transporter ("SERT" in FIG. 1 and the same shall apply hereinafter) and (2) flows out to the blood stream mediated by an organic anion transporter or others after being subjected to metabolic deactivation by 5HIAA by actions of monoamine oxidase ("MAO" in FIG. 1 and the same shall apply hereinafter). It is known that, in the brain, serotonin metabolism (biosynthesis, release, reuptake, metabolic deactivation and flowing into the blood stream) is repeated in a cyclic manner and its metabolic turnover is fast.

As described earlier, some aromatic monoamines are present in peripheral cells, etc., are present in neurons of the central nervous system. Aromatic monoamines in the brain are in principle do novo synthesized and metabolized therein without passing through the blood-brain barrier.

That is, aromatic monoamines in the brain are biosynthesized and accumulated in neurons in the brain. Release of aromatic monoamines into perineural cavities, reuptake into the neurons and metabolic deactivation is also carried out in the brain. Metabolic deactivation is carried out primarily in glia cells and partially in neurons.

Therefore, it is thought that active aromatic monoamines in the brain will not flow out into periphery as they are after being released from neurons but will flow out to peripheries after metabolic deactivation. It is also thought that peripheral aromatic monoamines will not migrate to the brain or reach neurons in the brain or perineural cavities. That is, a mere increase in serotonin at a periphery, for example, in urine, does not necessarily indicate an increase in serotonin in the brain.

In general, it is thought that an appropriate level of aromatic monoamines in the brain is determined by a balance of various factors such as the rate of biosynthesis in the brain, accumulation at releasing granules, synaptic release into pericellular cavities by neurons, reuptake and metabolic deactivation.

Tetrahydrobiopterin (BH4) is a coenzyme which is essential in action of tryptophan hydroxylase (TPH). Tetrahydrobiopterin (BH4) is capable of passing through a blood vessel wall in the blood-brain barrier at a rate similar to 5-hydroxytryptophan (5HTP) but is taken up very little by glia cells, etc., present in a perineural cavity. Furthermore, since tetrahydrobiopterin (BH4) is present substantially at a constant level in neurons, it is taken up very little into the neurons even when elevation of the concentration of tetrahydrobiopterin (BH4) elevates near the neurons. Therefore, as shown in FIG. 1, it is thought that the majority of tetrahydrobiopterin (BH4) is not taken up into glia cells or neurons after reaching the vicinity of the neurons and thereafter finally returns to the blood stream in the brain.

As shown in FIG. 1, sepiapterin ("SP" in FIG. 1 and the same shall apply hereinafter) is peripherally administered, passes through the blood-brain barrier after reaching the brain by the blood stream and is taken up into a monoaminergic neuron. In the monoaminergic neuron, sepiapterin is converted to tetrahydrobiopterin (BH4) via dihydrobiopterin ("BH2" in FIG. 1) and facilitates biosynthesis of serotonin and release thereof as a coenzyme of tryptophan hydroxylase (TPH) which is the rate limiting enzyme.

Sepiapterin (SP) passes through the blood vessel wall in the blood-brain barrier at a rate substantially similar to 5-hydroxytryptophan (5HTP) and is also taken up by glia cells, etc., present at a perineural cavity 10 times or more efficiently than tetrahydrobiopterin (BH4). Therefore, sepiapterin (SP) is thought to reach neurons in a greater amount than tetrahydrobiopterin (BH4).

Moreover, sepiapterin (SP) is readily converted to tetrahydrobiopterin (BH4) via dihydrobiopterin (BH2) after being taken up into a neuron. Therefore, sepiapterin in the neuron is kept relatively low in concentration. As a result, sepiapterin is continuously further taken up by the amount which has been converted to tetrahydrobiopterin (BH4). Thus, sepiapterin is thought to be taken up into the neuron in a greater amount than tetrahydrobiopterin (BH4).

When the above findings are comprehensively taken into account, peripheral supply of sepiapterin (SP) makes it possible to keep tetrahydrobiopterin (BH4) in a neuron in a greater amount than peripheral supply of tetrahydrobiopterin (BH4). Therefore, it is possible to activate tryptophan hydroxylase (TPH) more effectively and facilitate the biosynthesis of serotonin and release thereof.

Drugs such as an SSRI and an SNRI are those which increase the level of serotonin at a perineural cavity in the brain by inhibiting reuptake of serotonin by a serotonin transporter (SERT). Furthermore, a monoamine oxidase inhibitor is a drug which increases the level of serotonin in the brain by suppressing metabolic deactivation caused by monoamine oxidase (MAO).

<Drug of the Present Invention>

The present invention covers a wide variety of drugs which contain at least one of sepiapterin and its salt for preventing, improving and treating cerebral dysfunction.

As described above, sepiapterin means 7,8-dihydro-6-[(S)-2-hydroxy-1-oxopropyl]-pterin. An oxo group present in a substituent arranged in the 6-position of pterin may play an important role in allowing sepiapterin to pass through the blood-brain barrier. Therefore, if such a structure is kept that the oxo group is retained in the substituent to effect intracellular conversion to tetrahydrobiopterin, any drug, the structure of which is partially modified, is also included in sepiapterin of the present invention.

For example, isosepiapterin (7,8-dihydro-6-[(S)-2-oxo-1-hydroxypropyl]-pterin) is different in position of an oxo group but has an oxo group in the substituent, as with sepiapterin, and also maintains a structure which can be converted to tetrahydrobiopterin by actions of enzymes in the body such as sepiapterin reductase, aldose reductase and dihydrofolate reductase. Therefore, in the present invention, isosepiapterin is included in sepiapterin of the present invention as a compound similar to sepiapterin.

The drug of the present invention includes not only sepiapterin in itself and similar products (such as isosepiapterin) but also pharmaceutically acceptable salts and solvates. The salts include alkaline metal salts (such as sodium salt, potassium salt and lithium salt), alkaline earth metal salts (such as calcium salt, magnesium salt and lithium salt), metal salts (such as aluminum salt, iron salt, zinc salt, copper salt and nickel salt), inorganic salts (such as phosphate, sulfate, hydrobromate, ammonium salt), organic acid salts (such as methanesulfonate, p-toluenesulfonate, lactate, acetate, trifluoroacetate, citrate, succinate, fumarate, maleate and salicylate), organic amine salts (such as methylamine salt, dimethylamine salt, trimethylamine salt, ethylenediamine salt, diethylamine salt, triethylamine salt, ethanolamine salt, diethanolamine salt, dibenzylamine salt, glucosamine salt, dicyclohexylamine salt and tetramethylammonium salt), amino acid salts (such as glycine salt, lysine salt, arginine salt, ornithine salt and asparagine salt) and other organic salts (such as piperidine salt, morpholine salt, tris-(2-hydroxyl-ethyl) amine salt and choline hydrate).

The drug of the present invention also includes a prodrug composed of a compound having at least one of the protective groups which are pharmacologically acceptable and dissociable under physiological conditions. The prodrug is made available by a publicly known method (for example, refer to Non-Patent Document 6). The prodrug is made available by adding free carboxylic acid, an alkoxy group (for example, ethoxy group), phenalkyloxy group (for example, benzyloxy group), $OCH(R^a)OCOR^b$ group (for example, pivaloyloxymethyloxy group), $OCH(R^a)OCO_2R^b$ group (for example, [[(1-methylethoxy) carbonyl] oxy] ethylester group and proxetil group), $OCH(R^a)OR^b$ group, 2-alkyl group, 2-cycloalkyl group, 2-cycloalkyl alkyl group, oxycarbonyl-2-alkylidene-ethoxy group, 5-alkyl [1,3] dioxyl-2-on-oil-methyloxy group, dialkylamino-alkoxyl group, and acryloxy group ($R^a$ is a hydrogen atom or ($C_1$-$C_4$) alkyl group, and $R^b$ is any one of a hydrogen atom, ($C_1$-$C_6$) alkyl group, ($C_2$-$C_6$) alkenyl group, ($C_1$-$C_6$) alkoxy-($C_1$-$C_6$) alkyl group, ($C_1$-$C_6$) haloalkoxy-($C_1$-$C_6$) alkyl group, ($C_3$-$C_6$) cycloalkyl group, or ($C_3$-$C_6$) cycloalkylmethyl group). Moreover, where a free-form hydroxyl group is present in the structure, a protective group such as sulphate ($OSO_3H$), phosphate ($OPO_3H_3$), oxymethylene phosphate ($OCH_2OPO_3H_3$), succinate ester ($OCOCH_3CH_3COOH$), ester of dimethylaminoglycine, a natural amino acid, an inorganic salt or others is added to make the prodrug available.

The drug of the present invention is not in particular restricted to the dosage form. The drug is available, for example, in solid preparations (such as tablets, capsules, granules, powders, and sustained-release tablets) and liquid preparations (such as syrups and injections).

A carrier which is pharmacologically acceptable may be used to formulate a compound of the present invention into a drug. The carrier includes a variety of organic and inorganic carrier substances which are commonly used as pharmaceutical ingredients.

For example, in solid preparations, a diluting agent, a smoothing agent, a binder, a disintegrating agent, etc., are formulated into the drug of the present invention and its carrier. In liquid preparations, a solvent, a solubilizing agent, a suspending agent, an isotonic agent, a buffering agent, a soothing agent, etc., are appropriately formulated into the drug of the present invention and its carrier. Also, pharmaceutical additives such as an antiseptic, an antioxidant agent, a coloring agent and a sweetening agent may be added whenever necessary.

A preferable diluting agent includes, for example, lactose, sucrose, D-mannitol, starch, crystalline cellulose and light silicic anhydride.

A preferable smoothing agent includes, for example, magnesium stearate, calcium stearate, talc and colloidal silica.

A preferable binder includes, for example, crystalline cellulose, sucrose, D-mannitol, dextrin, hydroxypropyl cellulose, hydroxypropylmethyl cellulose and polyvinyl pyrrolidone.

A preferable disintegrating agent includes, for example, starch, carboxymethyl cellulose, carboxymethyl cellulose calcium, croscarmellose sodium and sodium carboxylmethyl starch.

A preferable solvent includes, for example, injection solvent, alcohol, propylene glycol, macrogol, sesame oil and corn oil.

A preferable solubilizing agent includes, for example, polyethylene glycol, propylene glycol, D-mannitol, benzyl benzoate, ethanol, trisaminomethane, cholesterol, triethanolamine, sodium carbonate and sodium citrate.

A preferable suspending agent includes, for example, surface active agents (such as stearyltriethanolamine, sodium lauryl sulfate, laurylamino propionate, lecithin, benzalkonium chloride, benzethonium chloride and glyceryl monostearate) and hydrophilic high polymers (such as polyvinyl alcohol, polyvinyl pyrrolidone, sodium carboxymethyl cellulose, methylcellulose, hydroxymethyl cellulose, hydroxyethyl cellulose and hydroxypropyl cellulose).

A preferable isotonic agent includes, for example, sodium chloride, glycerin and D-mannitol.

A preferable buffering agent includes, for example, buffering solutions of phosphate, acetate, carbonate, citrate, etc.

A preferable soothing agent includes, for example, benzyl alcohol.

A preferable antiseptic includes, for example, p-parahydroxybenzoate esters, chlorobutanol, benzyl alcohol, phenethyl alcohol, dehydroacetic acid and sorbic acid.

A preferable antioxidant agent includes, for example, sulfite and ascorbic acid.

In addition, the drug of the present invention may contain auxiliaries, for example, a light absorption pigment helpful in storage and efficacy retention (such as riboflavin, adenine and adenosine), a chelating agent/reducing agent for stabilization (such as vitamin C and citric acid), an amino acid substrate which enhances effects of sepiapterin in the brain (such as tryptophan) and analogous substances (such as tetrahydrobiopterin and dihydrobiopterin).

Although depending on its dosage form, route of administration and carrier, the drug of the present invention can be produced according to common procedures in which sepiapterin is allowed to be contained usually in a range of 0.1 to 99% (w/w) with respect to a total amount of formulation.

<Indications and Dosage Regimen of the Drug of the Present Invention>

The indications are not in particular restricted and may include any type of cerebral dysfunction which is decreased in the intracellular level of aromatic monoamines in the brain.

The above-described diseases include, for example, any one of the central mental disorders such as depression, hyperphagia, autism, impaired consciousness and concentration, and cognitive disturbance, or central motor disorders such as myotonia, rigidity and tremor. Cerebral dysfunction may be prevented, improved and treated by, for example, administration of sepiapterin at an effective dose to patients with cerebral dysfunction.

The drug of the present invention is applicable to mammals (for example, humans, horses, cattle, dogs, cats, rats, mice, pigs and monkeys).

The drug can be administered orally, for example, as tablets, capsules (including soft capsules and micro-capsules), powders and granules, or parenterally as injections, suppositories and pellets. Parenteral administration includes intravenous, intramuscular, subcutaneous, intraorgan, intranasal, intradermal, eye drop, intracerebral, intrarectal, vaginal and intraperitoneal administrations.

The drug of the present invention varies in dosage, depending on an administration route and symptoms. On intravenous administration to a patient, the drug is administered once daily at a dose of 0.1 to 100 mg/kg×the body weight. For example, the drug is given at this dose once daily or in one to three divided doses.

The drug of the present invention may be administered solely or concomitantly with other drugs, depending on the aim, usage or symptoms. For example, an SSRI and an SNRI have certain medicinal benefits. However, there is a risk that aromatic monoamines may be decreased in amount on long-term administration. On the other hand, it may be possible to obtain synergetic effects on concomitant administration of the drug of the present invention and these drugs.

It may also be possible to improve effects of sepiapterin in combination with, for example, an inhibitor of a retrograde transporter which prevents intracerebral migration of sepiapterin or an inhibitor of an extravert transporter which shortens the retention time of tetrahydrobiopterin in the brain by administration of sepiapterin.

Moreover, it is known that probenecid which is a renal excretion-type inhibitor is capable of prolonging in vivo retention of tetrahydrobiopterin at the peripheries. Therefore, it may be possible to increase the effect or prolong the retention time by using the drug of the present invention together with the renal excretion-type inhibitor.

The renal excretion-type inhibitor includes, for example, probenecid, immunomodulators (such as cyclosporine A, FK506 and thymosin $\alpha$-1), cytokines (such as TNF and TGF-$\beta$), interferons (IFN-$\alpha$, IFN-$\beta$, IFN-$\gamma$), interleukins (such as interleukins 1, 2, 3, 4, 5, 6, 7, 8, 10, 12, 13), macrophage/granular cell colony stimulating factors (such as GM-CSF, G-CSF and M-CSF), erythropoietin, cytokine antagonists (such as reticulose, ADA, AMD-3100, anti-TNF antibody, anti-interleukin antibody, soluble interleukin receptor and proteinkinase C inhibitor), nucleotide transporting inhibitors (such as dipyridamole, pentoxifylline, N-acetylcysteine (NAC), procysteine, $\alpha$-trichosanthin, phosphonoformic acid, dilazep and nitrobenzyl thioinosine), non-nucleotide reverse transcriptase inhibitors (NNRTIs; nevirapine, loviride, delavirdine, calanolide A, DPC-083, efavirenz, MKC-442 and capravirine), gp120 antagonists (such as PRO-2000, PRO542 and FP21399), and integrase inhibitors (such as T-20 and T-1249).

<Food/Drink of the Present Invention>

The present invention includes any food/drink for preventing, improving and treating cerebral dysfunction which contains at least one of sepiapterin and its salt as an active ingredient.

Sepiapterin and its salt are allowed to contain in, for example, health-promoting food (such as specified health-promoting food and food with nutrient function claims), that is, so-called health-conscious food/drink and other various types of food/drink. Furthermore, sepiapterin and its salt can be formulated into various types of seasoning, etc.

The food/drink is not in particular restricted to its form and may be available in liquid, half-solid and solid products. Specifically, it may be available, for example, as confectionery such as cookies, senbei (rice cracker), jelly, yokan (sweat jelly of beans), yogurt and manjyu (bean-jam filled bun), refreshing drinks, energy drinks and soups. It may also be available as a tea by infusion. Furthermore, the above-described drug may be added by mixture, coating or spraying, for example, in the process of manufacturing the food/drink of the present invention or to final products, thereby providing a health-conscious food/drink. Still furthermore, it may be allowed to be contained in a product that is temporarily kept in the mouth, for example, toothpaste, breath fresheners, chewing gum and mouthwash.

<Method for Producing the Drug of the Present Invention>

Sepiapterin of the present invention can be produced in accordance with a publicly known method. And, the method thereof is not restricted in particular.

For example, it is possible to produce tetrahydrobiopterin according to procedures in which the 6th-class diastereomer mixture (6R/6S mixture) is subjected to organic synthesis and 6R is subjected to chiral separation and purification.

Sepiapterin is also produced by utilizing the above synthesis system on the basis of organic synthesis. That is, a mixture of tetrahydrobiopterin with the 6th-class diastereomer (6R/6S) is synthesized, thereafter, the mixture is oxidized to produce a crude sepiapterin sample, and the sample is purified to produce sepiapterin (as for an example of the sepiapterin synthesizing method, refer to Non-Patent Document 7, for example). It is noted that, unlike tetrahydrobiopterin, since sepiapterin bears achiral in the 6th-class, it is possible to omit the step of chiral separation in a method for producing sepiapterin.

[Example 1]

In Example 1, where PC12 cells and RBL2H3 cells were used as aromatic monoamine synthesizing cells and sepiapterin was added to a culture medium, evaluation was made for a total amount of biopterin in the cells (a total amount of tetrahydrobiopterin, and its oxidant, dihydrobiopterin and biopterin, the same shall apply hereinafter).

The PC12 cells are cultured cells having properties of a neuron and it is known that they synthesize dopamine, noradrenaline and adrenaline, with tetrahydrobiopterin used as a coenzyme. The RBL2H3 cells are cultured cells having properties of a mast cell and it is known that they synthesize serotonin, with tetrahydrobiopterin used as a coenzyme.

The both cells are capable of synthesizing tetrahydrobiopterin and also retain a certain amount of tetrahydrobiopterin in the cells but do not retain a saturated amount thereof. Furthermore, unlike cells which are not capable of synthesizing aromatic monoamines by themselves but take up aromatic monoamines extracellularly and capable of secreting aromatic monoamines in response to stimulation (for example, platelets are not capable of synthesizing serotonin by themselves but take up serotonin extracellularly and are capable of secreting serotonin in response to stimulation), both cells are capable of synthesizing aromatic monoamines by themselves. In the present example, the inventor, etc., judged that these cells were suitable as models of aromatic monoamine synthetic cells and used them accordingly.

The PC12 cells and the RBL2H3 cells were obtained from the JCRB Cell Bank (National Institute of Biomedical Innovation, Japan).

The PC12 cells were sub-cultured in a DMEM medium (Dulbecco's Modified Eagle Medium; Dulbecco's medium, and the same shall apply hereinafter) containing 7% bovine fetal serum and 7% horse serum. In an experiment, the cells were plated on a 96-well polylysine-coated plate at $2 \times 10^5$ per well, the culture medium was replaced by a serum-free DMEM medium one hour before start of the experiment on the following day to carry out the following uptake experiment.

The RBL2H3 cells were cultured in a DMEM medium containing 10% bovine fetal serum and plated on a 96-well coating-free plate at $1 \times 10^5$ per well. Similarly, one hour before start of the experiment on the following day, the culture medium was replaced by a serum-free DMEM medium to carry out the following uptake experiment.

Sepiapterin or tetrahydrobiopterin was added to the respective media of the PC12 cell and the RBL2H3 cell so as to give a final concentration of 100 µM. At 0, 30, 60, 120, and 180 minutes later, the media were washed quickly three times by using an ice-cold physiological saline (PBS (+): phosphate buffered saline containing $Ca^{2+}$, $mg^{2+}$) to measure a total amount of biopterin in the respective cells (n=6 each).

A total amount of biopterin in the cells was measured by using a system of high performance liquid chromatography/fluorescence detection (HPLC/FD) according to the Fukusima-Nixon method (refer to Non-Patent Document 8).

A principle of the Fukushima-Nixon method is as follows. Upon oxidation with iodine under strong acid or alkaline conditions, tetrahydrobiopterin is quantitatively oxidized into oxidized-form biopterin under acid conditions and oxidized into oxidized-form pterin in which a side chain in the 6th-class position is removed under alkaline conditions. Dihydrobiopterin is oxidized into oxidized-form biopterin irrespective of pH conditions. The oxidized-form biopterin and the oxidized-form pterin have strong natural fluorescent characteristics (excitation: 350 nm, fluorescence: 450 nm). Therefore, the same sample is divided into two portions, and one of them and the other are oxidized with iodine respectively under acid conditions and alkaline conditions. An amount of the oxidized-form biopterin is compared with that of the oxidized-form pterin on fluorescence detection after quantitative determination, thus making it possible to determine the respective amounts of tetrahydrobiopterin and dihydrobiopterin in an original sample.

The thus prepared sample was used in the system of high performance liquid chromatography/fluorescence detection. And, the oxidized-form biopterin and the oxidized-form pterin were quantitatively determined according to an external standard comparison method. Then, calculated was an amount of tetrahydrobiopterin and a total amount of biopterin in the cells. In the high performance liquid chromatography, "Fine-SIL-C18-5T (made by JASCO Corporation)" was used as a column, and a 7% aqueous methanol solution was used as an eluent. An FP model made by JASCO Corporation was used to carry out fluorescence detection.

The respective cells used in the present example contain by nature oxidized-form biopterin and oxidized-form pterin only in a trace amount. The experiment was done on the assumption that they were not present.

Sepiapterin is not metabolized in the cells by uptake in a period of time during which the experiment was performed except for dihydrobiopterin, irrespective of whether it is exogenous or endogenous. Dihydrobiopterin in the cells is reduced by dihydrofolate reductase to tetrahydrobiopterin but some of dihydrobiopterin remains in the cells. It is found that reactions other than reduction of dihydrobiopterin to tetrahydrobiopterin and decomposition of tetrahydrobiopterin hardly take place in a period of time during which the experiment was performed. It is also clear that sepiapterin is capable of migrating from inside to outside of the cells and vice versa, dihydrobiopterin is capable of migrating in the above-described manner only slightly, and tetrahydrobiopterin is hardly capable of migrating in the above-described manner (Non-Patent Document 1). On the basis of the above findings, a sum of the amount of dihydrobiopterin and the amount of tetrahydrobiopterin was given a total amount of biopterin in the cells.

FIG. 2A and FIG. 2B show the results. FIG. 2A is a graph which shows the change in the total amount of biopterin in the PC12 cells with the lapse of time, and FIG. 2B is a graph which shows a change in the total amount of biopterin in the RBL2H3 cells with the lapse of time. In each of the graphs, a longitudinal axis indicates the number of moles of a total amount of biopterin per cell population $1 \times 10^6$ (total BP, unit: nmol/$10^6$ cells), while a horizontal axis indicates time after addition of sepiapterin or tetrahydrobiopterin (Time, unit: min). In each of the graphs, black circles indicate results obtained when sepiapterin (SP) was added, and white circles indicate results obtained when tetrahydrobiopterin (BH4) was added. An error bar indicates a standard deviation (the same shall apply hereinafter). Results free of the error bar are smaller in size than a symbol (the same shall apply hereinafter).

As shown in FIG. 2A and FIG. 2B, in the respective cells, there was observed a remarkable increase in the total amount of biopterin in the cells on addition of sepiapterin. However, there was observed substantially no change in the total amount of biopterin in the cells on addition of tetrahydrobiopterin. The results show a continuous increase in the total amount of biopterin in aromatic-monoamine secreting cells on addition of sepiapterin. The results also show essentially no change in the total amount of biopterin in the aromatic-monoamine secreting cells on addition of tetrahydrobiopterin.

There was observed a slight increase in the total amount of biopterin on addition of tetrahydrobiopterin. This was due to the fact that tetrahydrobiopterin oxidized in a culture medium under experiment conditions was turned into dihydrobiopterin and taken up secondarily (refer to Non-Patent Document 1). Furthermore, biopterin in the cells was made up of 95% of tetrahydrobiopterin and remaining percentages of dihydrobiopterin.

When the above results are comprehensively taken into account, tetrahydrobiopterin was hardly taken up into aromatic monoamine synthetic cells on addition of tetrahydrobiopterin, and there was observed substantially no change in the total amount of biopterin in the cells. On the other hand, sepiapterin was taken up into the aromatic monoamine synthetic cells on addition of sepiapterin and converted to tetrahydrobiopterin in the cells, therein the total amount of biopterin was increased in the cells.

That is, the results of the present example have suggested that, on peripheral administration of sepiapterin to animals including humans, unlike tetrahydrobiopterin, sepiapterin passes through the cell membrane of an aromatic monoamine neuron after passing through the blood-brain barrier. And, sepiapterin is taken up into the cells and converted to tetrahydrobiopterin in the cells, thereby facilitating biosynthesis of aromatic monoamines.

[Example 2]

In Example 2, a cell system of a brain blood vessel wall model was used to compare passage of sepiapterin with that of tetrahydrobiopterin across a blood vessel wall.

As the brain blood vessel wall model, there was used a "BBB kit, RBT24H (made by PharmaCo-Cell Company Ltd. in Japan)." This kit was a model system in which rat vascular endothelical cells were cultured on a porous synthetic resin film having small pores of 3 μm in inner diameter to form tight intercellular junctions, thereby forming the blood vessel wall. In this kit, pericytes were cultured in advance on the back side of the porous synthetic resin film and astroglia cells were also cultured at the same time in the well below the film, thereby forming the intercellular tight junctions of vascular endothelical cells. A cultured area was 0.3 cm$^2$ per well. In this model, the cell sheet, an upper side of the cell sheet and a lower side of the cell sheet respectively correspond to the blood vessel wall, an intravascular cavity (lumen) and a perineural cavity in the brain (albumen).

According to an attached manufacture's instruction, each of tetrahydrobiopterin (BH4), sepiapterin (SP) and 5-hydroxytryptophan (5HTP) was dissolved in the upper side of the cell sheet corresponding to the intravascular lumen by using a physiological balanced salt and added at a concentration of 100 μM. After 30 minutes, each of them was measured for an amount which migrated downward to the cell sheet.

An amount of tetrahydrobiopterin (BH4) was calculated according to the method described in Example 1.

An amount of sepiapterin (SP) was calculated according to an external standard comparison method by treating samples by a system of high performance liquid chromatography/fluorescence detection. In the high performance liquid chromatography, as with Example 1, "Fine-SIL-C18-5T (made by JASCO Corporation)" was used as a column, and a 14% aqueous methanol solution was used as an eluent. Fluorescence detection was carried out by setting the exciting wavelength and the fluorescence wavelength to be 412 nm and 527 nm respectively to make measurement using an FP model made by JASCO Corporation.

An amount of 5-hydroxytryptophan (5HTP) was calculated according to an internal standard comparison method using N-methyl serotonin by treating samples in the system of high performance liquid chromatography/fluorescence detection (refer to Non-Patent Document 9). In the high performance liquid chromatography, as with Example 1, "Fine-SIL-C18-5T (made by JASCO Corporation)" was used as a column. Formic acid was added to a 40 mM aqueous sodium acetate solution, thereby adjusting pH to 3.5, and the aqueous sodium acetate solution, acetonitrile and methanol were mixed in a volume ratio of 100:10:5 to prepare a solution, and the solution was used as an eluent. Fluorescence detection was carried out by setting the exciting wavelength and the fluorescence wavelength to be 302 nm and 350 nm respectively to make measurement using an FP model made by JASCO Corporation.

As described earlier, 5-hydroxytryptophan (6HTP) is a substance which is now used as a drug of the first choice on peripheral administration to patients with tetrahydrobiopterin deficiency for the purpose of increasing the amount of serotonin in the brain.

FIG. 3 shows the results. FIG. 3 is a graph which shows an amount of downward migration of each of tetrahydrobiopterin (BH4), sepiapterin (SP) and 5-hydroxytryptophan (5HTP) added over the upper side of the cell sheet of the brain blood vessel wall model. In FIG. 3, a horizontal axis indicates the respective results on addition of tetrahydrobiopterin (BH4), sepiapterin (SP) and 5-hydroxytryptophan (5HTP), and a longitudinal axis indicates the amount of downward migration to the lower face of the cell sheet (unit: pmol/well/30 min). Each value was subjected to the Student t-test ($p<0.05$).

As shown in FIG. 3, although a significant difference was observed, tetrahydrobiopterin (BH4) and sepiapterin (SP) were similar to 5-hydroxytryptophan (5HTP) in the amount of migration to the lower side of the cell sheet. That is, the results have suggested that tetrahydrobiopterin (BH4) and sepiapterin (SP) are capable of passing through blood vessel walls which constitute the blood-brain barrier at a rate substantially similar to 5-hydroxytryptophan (5HTP).

[Example 3]

In Example 3, comparison was made between sepiapterin and tetrahydrobiopterin in terms of uptake into astroglia cells.

The astroglia cells are major glia cells and present tightly around vessels of the brain. This cell selectively takes up a substance which has passed through the blood vessel walls of the brain and supplies the substance to neurons.

Therefore, CTX TNA2 cells, that is, cultured cells derived from the astroglia cells, were used to evaluate the uptake of sepiapterin and that of tetrahydrobiopterin into the astroglia cells. It is noted that the CTX TNA2 cells used were obtained from the ATCC in the U.S.A. (American Type Culture Collection).

On a previous day of the experiment, the CTX TNA2 cells were inoculated at $1 \times 10^5$ per well. Thirty minutes after a culture medium was replaced by Hank's-HEPES (pH 7.4), sepiapterin was added at 50 μM or tetrahydrobiopterin was added at 100 μM, each of which was cultured for 0, 5, 10, 20, 40 and 60 minutes. After cultivation for the above-described period of time, the culture medium was removed to quantitatively determine an amount of each of sepiapterin (SP), dihydrobiopterin (BH2) and tetrahydrobiopterin (BH4) (n=5 each) accumulated in the cells according to the method described in Example 1 or Example 2.

FIG. 4A and FIG. 4B show the results. FIG. 4A is a graph which shows the amounts of sepiapterin (SP), dihydrobiopterin (BH2) and tetrahydrobiopterin (BH4) accumulated in the cells on addition of sepiapterin (SP). FIG. 4B is a graph which shows the amounts of dihydrobiopterin (BH2) and tetrahydrobiopterin (BH4) on addition of tetrahydrobiopterin (BH4). In each of the graphs, a horizontal axis indicates cultivation time after addition of sepiapterin or tetrahydrobiopterin. A longitudinal axis indicates the amounts of sepiapterin (SP), dihydrobiopterin (BH2) and tetrahydrobiopterin (BH4) which were quantitatively determined (unit: pmol/$10^6$ cells).

As shown in FIG. 4A and FIG. 4B, when addition of sepiapterin (SP) (FIG. 4A) was compared with addition of tetrahydrobiopterin (BH4) (FIG. 4B), it was revealed that the amount of tetrahydrobiopterin (BH4) accumulated in the cultured cells was at least 10 times greater on addition of sepiapterin than on addition of tetrahydrobiopterin. And, this amount was at least 20 times greater on conversion of an added amount to the same concentration.

The above results have suggested that sepiapterin is taken up more easily into glia cells 10 times or more than tetrahydrobiopterin, and tetrahydrobiopterin (BH4) is rapidly synthesized in the glia cells via dihydrobiopterin (BH2) from sepiapterin (SP) taken up into the glia cells.

As described above, the blood-brain barrier is primarily formed with blood vessel walls and glia cells. Astrocytes, a major type of glia cell, selectively take up a substance which has passed through blood vessel walls of the brain and supply the substance to neurons. Therefore, it is thought that the substance which has passed through the blood vessel walls and has been taken up by astroglia cells will reach neurons.

The results of Example 2 and the present example revealed that sepiapterin was substantially similar to tetrahydrobiopterin in amount which has passed through the blood vessel walls further sepiapterin was at least 10 times greater in amount taken up in glia cells than tetrahydrobiopterin.

Therefore, the above results have suggested that sepiapterin passes through the blood-brain barrier at least 10 times more easily than tetrahydrobiopterin. That is, when the results of Example 1 are also taken into account, sepiapterin passes through the blood-brain barrier more easily than tetrahydrobiopterin on peripheral administration and is also easily taken up by aromatic monoamine neurons.

[Example 4]

In Example 4, rats were used to measure amounts of tetrahydrobiopterin, serotonin and 5-hydroxyindoleacetic acid in the brain on administration of sepiapterin.

Here, 5-hydroxyindoleacetic acid, which is a metabolic product of serotonin, is thought to be metabolized and converted from serotonin mainly in glia cells or serotonin-producing cells. In this experiment, 5-hydroxyindoleacetic acid was also measured as an index of the bioavailability of an aromatic monoamine (serotonin) in the brain.

Rats used were SD rats (7-8 week old, males) purchased from Japan SLC, Inc. The rats were kept in a dark place for 12 hours and in a light place for 12 hours and fed ad libitum with a diet ("MM-3" made by Funabashi Farm Co., Ltd.) and sterilized tap water as drinking water.

Sepiapterin or tetrahydrobiopterin was dissolved in 10 mM hydrochloric acid, the resultant of which was orally administered to the rats (n=6) under diethylether anesthesia. After 1, 1.5, 2, 3, 4, 6 and 8 hours, the brains were excised under pentobarbital sodium anesthesia (pentobarbital was intraperitoneally administered at 40 mg/kg five minutes before), and the brain was divided into two portions at the median line to obtain left and right brain samples. Rats not treated with sepiapterin or tetrahydrobiopterin were used as samples at 0 hours after administration according to the same procedures.

An amount of tetrahydrobiopterin in the brain was measured and calculated according to a method similar to Example 1 by adding 5 times the volume of 100 mM hydrochloric acid to a left brain sample, homogenizing brain tissues and utilized the supernatant solution.

Amounts of serotonin and 5-hydroxyindoleacetic acid in the brain were calculated by adding 3.5 times the volume of 1.43% ascorbic acid-containing 100 mM hydrochloric acid which contains N-methyl serotonin as an internal standard to a right brain sample, homogenizing brain tissues, adding potassium perchlorate (final concentration of 5.5%) thereto, ice-cooling the resultant for removing protein and treating a supernatant thereof in a system of high performance liquid chromatography/fluorescence detection (HPLC/FD), (refer to Non-Patent Document 9). In the high performance liquid chromatography, as with Example 1, etc., "Fine-SIL-C18-5T (made by JASCO Corporation)" was used as a column. As with Example 2, formic acid was added to a 40 mM aqueous sodium acetate solution, thereby adjusting pH to 3.5. Then, the aqueous sodium acetate solution, acetonitrile and methanol were mixed in a volume ratio of 100:10:5 to prepare a solution, and the solution was used as an eluent. As with Example 1, etc., fluorescence detection was carried out by setting the exciting wavelength and the fluorescence wavelength to be 302 nm and 350 nm respectively and making measurement using an FP model made by JASCO Corporation. In the system of high performance liquid chromatography/fluorescence detection (HPLC/FD), 5-hydroxytryptophan (5HTP), serotonin, N-methyl serotonin, tryptophan and 5-hydroxyindoleacetic acid are eluted in the above order, thus making it possible to determine quantitatively these substances at the same time.

The results are shown in FIG. 5A, FIG. 5B, and FIG. 5C.

FIG. 5A is a graph which shows change in the amount of tetrahydrobiopterin in the brain with the lapse of time after administration of sepiapterin. In the graph, a longitudinal axis indicates an amount of tetrahydrobiopterin (BH4, unit: nmol/g brain), and a horizontal axis indicates time after administration of tetrahydrobiopterin or sepiapterin (time, unit: hour). In the graph, black circles indicate results on addition of sepiapterin (SP), and white circles indicate results on addition of tetrahydrobiopterin (BH4). The two-way analysis of variance revealed that a value obtained on administration of sepiapterin was statistically and significantly higher than a value obtained on administration of tetrahydrobiopterin over 1.5 to 6 hours after administration ($p<0.0001$).

As shown in FIG. 5A, a group treated with tetrahydrobiopterin did not show an increase in the amount of tetrahydrobiopterin in the brain, while a group treated with sepiapterin showed a significant increase in the amount of tetrahydrobiopterin in the brain.

The above results have shown that peripheral administration of sepiapterin increases the amount of tetrahydrobiopterin in the brain. The results have also shown that peripheral administration of tetrahydrobiopterin at the same dose does not increase the amount of tetrahydrobiopterin in the brain.

Of brain cells, approximately 90% or more are made up of non-neurons and the remaining part of approximately 10% is made up of neurons. Aromatic monoamine nerves occupy only a small portion of the remaining part. Therefore, all tetrahydrobiopterin which has been elevated in the brain does not necessarily account for an elevation thereof in aromatic monoamine neurons. However, as shown in Example 1, sepiapterin easily migrates to aromatic monoamine synthetic cells and is reduced to tetrahydrobiopterin in the cells. Furthermore, as shown in Non-Patent Document 1, it is known that sepiapterin enters into cells in the form of sepiapterin and is quickly reduced to tetrahydrobiopterin and also the tetrahydrobiopterin is retained for a relatively long period of time in the cells. As described above, of continuous elevation of tetrahydrobiopterin on administration of sepiapterin as shown in FIG. 5A, a substantial part of the elevation is estimated at a higher possibility to take place in the aromatic monoamine synthetic cells. Furthermore, administration of tetrahydrobiopterin at the same dose does not result in elevation of tetrahydrobiopterin in the brain, which is in compliance with the suggestion obtained from the results of Example 1 and content thereof.

Then, FIG. 5B is a graph which shows change in the amount of serotonin in the brain with the lapse of time after administration of sepiapterin. FIG. 5C is a graph which also shows change in the amount of 5-hydroxyindoleacetic acid (5HIAA) in the brain with the lapse of time. In each of the graphs, a horizontal axis indicates time from administration of tetrahydrobiopterin or sepiapterin (time, unit: hour) and a longitudinal axis indicates an amount of serotonin (5HT, unit: nmol/g brain) or that of 5-hydroxyindoleacetic acid (5HIAA, unit: nmol/g brain). In each of the graphs, black circles indicate results on addition of sepiapterin (SP) and white circles indicate results on administration of tetrahydrobiopterin (BH4). The two-way analysis of variance revealed that, in the above cases, a group treated with sepiapterin was significantly higher in the amount of serotonin than a group treated with tetrahydrobiopterin ($p<0.0001$).

As shown in FIG. 5B and FIG. 5C, in the group treated with tetrahydrobiopterin, serotonin and 5-hydroxyindoleacetic acid in the brain were not increased in amount over a long period of time. However, in the group treated with sepiapterin, serotonin in the brain was significantly increased in amount from three to eight hours and subsequently after administration.

The above results have suggested that on peripheral administration of sepiapterin, a part of sepiapterin goes beyond the blood-brain barrier to reach the brain, then, is taken up into neurons capable of synthesizing aromatic monoamines in the brain and converted to tetrahydrobiopterin, thus resulting in an increase in the amount of serotonin in the brain. Furthermore, peripheral administration of tetrahydrobiopterin at the same dose does not significantly increase the amount of serotonin in the brain, showing that tetrahydrobiopterin which has been peripherally administered does not substantially reach aromatic monoamine synthetic cells due to some hindrance. This result is well complemented by the results of FIG. 5A and not contradictory to the results of Example 1.

As described above, the results of Example 1 and the present experiment have strongly suggested a series of action mechanisms in which, on peripheral administration of sepiapterin, sepiapterin passes through the blood-brain barrier by a certain amount, reaches the brain, also passes through cell membranes of aromatic monoamine neurons, then, is taken up into aromatic monoamine neurons in the brain, converted to tetrahydrobiopterin in the neurons, and the tetrahydrobiopterin effectively contributes to the synthesis of serotonin, thereby increasing the amount of serotonin in the brain. The results have also suggested that peripheral administration of tetrahydrobiopterin at the same dose will not enhance the series of action mechanisms in the brain.

[Example 5]

In Example 5, mice were used to measure the amount of serotonin (5HT) in the brain after administration of sepiapterin.

The mice used were those of "hph-1" which were provided by Dr. K. Hyland (Institute of Metabolic Disease, Baylor University Medical Center, Dallas, Tex. 75226, USA). The mice are characterized as being defective in biosynthesis functions of tetrahydrobiopterin, with the level of tetrahydrobiopterin in the brain being from 40 to 50% as compared with ordinary mice. The mice were bred in a dark place for 12 hours and also in a light place for 12 hours and fed ad libitum with a diet ("MM-3" made by Funabashi Farm Co., Ltd.) and sterilized tap water as drinking water.

An amount of serotonin was measured by dissolving sepiapterin or tetrahydrobiopterin in 0.01 M hydrochloric acid, thereafter administering orally each of the resultants at 20 mg/kg to the mice, giving another oral administration at the same dose two hours thereafter, and excised the brains from each mouse six hours after the first administration (n=7 in a group treated with sepiapterin, and n=8 in a group treated with tetrahydrobiopterin). Measurement of the amount of serotonin was made by obtaining brain samples according to a method similar to Example 4, treating the samples in a system of high-performance liquid chromatography/fluorescence detection (HPLC/FD) after dissolution of the samples and protein removal from them, and setting the excited wavelength and the fluorescence wavelength to be 302 nm and 350 nm respectively. In a control group, measurement was made similarly by orally administering 0.01M hydrochloric acid.

FIG. 6 shows the results. FIG. 6 is a graph which shows the amount of serotonin in the brain after administration of sepiapterin. In the graph, a longitudinal axis indicates the amount of serotonin (5HT, unit: nmol/g brain), "v-cont" shows the results of a control group, "BH4" shows the results on administration of tetrahydrobiopterin and "SP" shows the result on administration of sepiapterin, respectively. In the graph, an asterisk shows a significant difference found by t-test ($p<0.05$).

As shown in FIG. 6, a group treated with sepiapterin showed a significant increase in serotonin in the brain as compared with a group treated with tetrahydrobiopterin. That is, the results show that, as with Example 4, a significant increase in the level of an aromatic monoamine in the brain (serotonin) was observed on administration of sepiapterin in the experiment with mice as well.

As described above, Example 4 and the present example showed that peripheral administration of sepiapterin increased the amount of serotonin in the brain but peripheral administration of tetrahydrobiopterin at the same dose did not increase the amount.

It is known that intracerebral biosynthesis, release, reuptake and metabolism of dopamine whose starting material is tyrosine of aromatic amino acid are also based on a synthesis amount of dopamine at dopaminergic neurons and dopamine biosynthesis is restricted by the amount of intracellular tetrahydrobiopterin. Therefore, the results of Example 4 and the present example have suggested that dopamine as well as noradrenaline and adrenaline synthesized from dopamine are also increased in intracerebral levels thereof on peripheral administration of sepiapterin. That is, the above results have suggested that peripheral administration of sepiapterin may also be effective in improving central mental disorders and central motor disorders which are involved in decreased levels of dopamine, noradrenaline and adrenaline in the brain.

[Example 6]

In Example 6, the mice were subjected to a forced swim test after administration of sepiapterin.

The forced swim test of the mice is a test method for evaluating antidepressant effects, and length of "immobile" time is a criterion of depression. Evaluation is made in such a manner that the shorter the "immobile" time is, the greater the antidepressant effects are.

The mice used were NZB mice purchased from. Japan SLC, Inc (7-week old males). The mice were maintained in a dark place for 12 hours and in a light place for 12 hours and fed ad libitum with a diet ("MM-3" made by Funabashi Farm Co., Ltd.) and sterilized tap water as drinking water, except when they were constrained in an experiment.

The mice are characterized in that they are more likely to develop an auto-immune disease with advancement of age. However, in the present experiment, the mice did not exhibit symptoms of the disease when being used in the experiment (7-week old). The mice which had been subjected to 15-minute preliminary swimming without administration of a drug, etc., on the previous day were used in the experiment.

The mice were intraperitoneally administered tetrahydrobiopterin (n=7) or sepiapterin (n=5) at a single dose of 10 mg/kg and subjected to a forced swim test after 40 minutes to measure "immobile" time. The test was conducted under dim light by using a 15 cm-across and 15 cm-deep water tank kept at a temperature of 22° C. "Immobile" time was measured by calculating an added value of "immobile" time during five-minute-swimming. A similar experiment was carried out by giving a physiological saline to a control group (n=5) and giving desipramine at 40 mg/kg to a positive control group (n=5). Desipramine, that is, a tricyclic antidepressant, was used because it was judged to be used appropriately as a positive control for demonstrating anti-depressant effects.

FIG. 7 shows the above results. FIG. 7 is a graph which shows "immobile" time after administration of sepiapterin in the mice forced swim test. In the graph, a longitudinal axis indicates "immobile" time (unit: min. during 5 min.), "control" indicates the result of the control group, "BH4" indicates the result on administration of tetrahydrobiopterin, "SP" indicates the result on administration of sepiapterin, and "Dsp" indicates the result on administration of desipramine to the positive control group. Furthermore, the t-test revealed a significant difference of p=0.005 between "control" and "SP" as well as a significant difference of p=0.004 between "BH4" and "SP." Furthermore, a difference between "SP" and "Dsp" was p=0.69, which was estimated not to be a significant difference in terms of statistics.

As shown in FIG. 7, a group treated with sepiapterin was significantly short in "immobile" time as compared with a group treated with tetrahydrobiopterin and the control group. Thus, anti-depressant effects were obtained. Furthermore, the group treated with sepiapterin was also effective in shortening "immobile" time to an extent similar to the positive control group.

As described above, the results of Examples 1 to 6 have suggested that tetrahydrobiopterin hardly reaches the brain or is not taken up into neurons on peripheral administration, thus resulting in no increase in the level of aromatic monoamines in the brain, and improvement in cerebral dysfunction can be hardly expected. On the other hand, sepiapterin partially reaches the brain and is easily taken up into neurons on peripheral administration, thus resulting in an increased level of aromatic monoamines in the brain, suggesting effectiveness in improving cerebral dysfunction.

Therefore, these results have suggested that the present invention is effective in preventing, improving and treating central mental disorders such as depression, hyperphagia, autism, impaired consciousness and concentration, and cognitive disturbance. In addition, biosynthesis of dopamine, noradrenaline and adrenaline depends on the level of tetrahydrobiopterin in the neurons, as with serotonin. Thus, the results have suggested that the present invention is effective in preventing, improving and treating central motor disorders such as myotonia, rigidity and tremor.

BRIEF DESCRIPTION OF THE DRAWINGS

FIG. 1 is an illustration which depicts a metabolic system of aromatic monoamine in neurons in a brain.

FIG. 2A is a graph which shows change in the total amount of biopterin taken up into PC12 cells with the lapse of time in Example 1.

FIG. 2B is a graph which shows change in the total amount of biopterin taken up into RBL2H3 cells with the lapse of time in Example 1.

FIG. 3 is a graph which shows an amount of downward migration of each of tetrahydrobiopterin (BH4), sepiapterin (SP) and 5-hydroxytryptophan (5HTP) added over the upper side of the cell sheet of the brain blood vessel wall model (RBT24H) in Example 2.

FIG. 4A is a graph which shows amounts of sepiapterin (SP), dihydrobiopterin (BH2) and tetrahydrobiopterin (BH4) accumulated in CTX, TNA2 cells on addition of sepiapterin (SP) in Example 3.

FIG. 4B is a graph which shows amounts of dihydrobiopterin (BH2) and tetrahydrobiopterin (BH4) accumulated in the CTX INA 2 cells on addition of tetrahydrobiopterin (BH4) in Example 3.

FIG. 5A is a graph which shows change in the amount of tetrahydrobiopterin in the brain with the lapse of time after administration of sepiapterin in an experiment with rats in Example 4.

FIG. 5B is a graph which shows change in the amount of serotonin in the brain with the lapse of time after administration of sepiapterin in the experiment with rats in Example 4.

FIG. 5C is a graph which shows change in the amount of 5-hydroxyindoleacetic acid in the brain after administration of sepiapterin in the experiment with rats in Example 4.

FIG. 6 is a graph which shows the amount of serotonin in the brain after administration of sepiapterin in an experiment with mice (hph-1) in Example 5.

FIG. 7 is a graph which shows "immobile" time after administration of sepiapterin in a forced swim test with mice (NZB) in Example 6.

The invention claimed is:

1. A method of preventing or improving cerebral dysfunction in a subject with a central motor disorder, the method comprising peripherally administering a composition which contains at least sepiapterin to the subject with cerebral dysfunction, wherein the central motor disorder is myotonia, and wherein the composition is administered in an amount sufficient to suppress a decrease in aromatic monoamines in the brain.

2. The method of claim 1, wherein the composition is a food or drink which contains sepiapterin as an active ingredient.

3. The method of claim 1, wherein the composition is administered at a dose of 0.1 to 100 mg/kg of sepiapterin.

4. The method of claim 1, wherein the aromatic monoamines comprise serotonin, dopamine, adrenaline, and/or noradrenaline.

5. The method of claim 1, wherein the composition is a food or drink which contains sepiapterin as an active ingredient.

6. The method of claim 1, wherein the composition is administered at a dose of 0.1 to 100 mg/kg of sepiapterin.

7. The method of claim 1, wherein the composition further comprises a pharmacologically acceptable carrier.

8. The method of claim 1, wherein the composition further comprises a pharmacologically acceptable carrier.

* * * * *